US010786515B2

(12) United States Patent
Downing et al.

(10) Patent No.: US 10,786,515 B2
(45) Date of Patent: Sep. 29, 2020

(54) LIQUID POLYMER DELIVERY SYSTEM FOR EXTENDED ADMINISTRATION OF DRUGS

(71) Applicant: TOLMAR INTERNATIONAL LIMITED, Dublin (IE)

(72) Inventors: John Milton Downing, Fort Collins, CO (US); Vipin Saxena, Carol Stream, IL (US); John Middleton, Fort Collins, CO (US)

(73) Assignee: Tolmar International Limited, Dublin (IE)

( * ) Notice: Subject to any disclaimer, the term of this patent is extended or adjusted under 35 U.S.C. 154(b) by 0 days.

(21) Appl. No.: 15/749,030

(22) PCT Filed: Aug. 3, 2016

(86) PCT No.: PCT/US2016/045334
§ 371 (c)(1),
(2) Date: Jan. 30, 2018

(87) PCT Pub. No.: WO2017/024027
PCT Pub. Date: Feb. 9, 2017

(65) Prior Publication Data
US 2018/0214459 A1    Aug. 2, 2018

Related U.S. Application Data

(60) Provisional application No. 62/200,198, filed on Aug. 3, 2015, provisional application No. 62/275,407, filed on Jan. 6, 2016.

(51) Int. Cl.
| | | |
|---|---|---|
| A61K 9/00 | (2006.01) | |
| A61K 47/00 | (2006.01) | |
| A61K 31/00 | (2006.01) | |
| A61P 5/26 | (2006.01) | |
| A61K 31/568 | (2006.01) | |
| A61K 47/34 | (2017.01) | |
| A61K 47/59 | (2017.01) | |
| A61K 38/09 | (2006.01) | |
| A61K 38/29 | (2006.01) | |
| A61K 38/00 | (2006.01) | |

(52) U.S. Cl.
CPC .......... *A61K 31/568* (2013.01); *A61K 9/0019* (2013.01); *A61K 9/0024* (2013.01); *A61K 38/09* (2013.01); *A61K 38/29* (2013.01); *A61K 47/34* (2013.01); *A61K 47/593* (2017.08); *A61P 5/26* (2018.01); *A61K 38/00* (2013.01)

(58) Field of Classification Search
None
See application file for complete search history.

(56) References Cited

U.S. PATENT DOCUMENTS

| | | |
|---|---|---|
| 5,278,201 A | 1/1994 | Dunn et al. |
| 5,668,288 A | 9/1997 | Storey et al. |
| 6,197,320 B1 | 3/2001 | Shalaby |
| 6,565,874 B1 | 5/2003 | Dunn et al. |
| 8,187,640 B2 | 5/2012 | Dunn |
| 8,470,359 B2 | 6/2013 | Dunn |
| 2009/0181068 A1 | 7/2009 | Dunn |

FOREIGN PATENT DOCUMENTS

| | | |
|---|---|---|
| WO | WO 02/30393 | 4/2002 |
| WO | WO 2009/060473 | 5/2009 |

OTHER PUBLICATIONS

Steele et al., Tuning drug release in polyester thin films: terminal end-groups determine specific rates of additive-free controlled drug release, NPG Asia Materials, 5, pp. 1-8. (Year: 2013).*
Lanao et al., Tissue Engineering: Part B, 19(4), pp. 380-390. (Year: 2013).*
International Preliminary Report on Patentability for International (PCT) Patent Application No. PCT/US2016/045334, dated Nov. 3, 2017 38 pages.
Official Action with English Translation for Eurasia Patent Application No. 201890436, dated Mar. 26, 2019 10 pages.
Official Action for European Patent Application No. 16751437.1, dated Dec. 19, 2018 7 pages.
International Search Report for International Patent Application No. PCT/US2016/045334, dated Oct. 14, 2016, 7 pages.
Written Opinion for International Patent Application No. PCT/US2016/045334, dated Oct. 14, 2016, 7 pages.
Second Written Opinion of the International Preliminary Examining Authority for International Patent Application No. PCT/US2016/045334, dated Jul. 13, 2017, 10 pages.
Perego et al. "Copolymers of L- and D,L-lactide with 6-caprolacton: synthesis and characterization," Makromol. Chem., 1993, vol. 194, pp. 2463-2469.
Zhang et al. "Biodegradation of In Situ-Forming Gel of Poly(DLLA-co-CL) In Vivo," Journal of Applied Polymer Science, Sep. 2013, vol. 130, No. 5, pp. 3800-3808.
Zhang et al. "Suppression of spermatogenesis by testosterone undecanoate-loaded injectable in situ-forming implants in adult male rats," Asian Journal of Andrology, 2016, vol. 18, pp. 791-797.
Zhang et al. "Feasibility of poly (ε-caprolactone-co-DL-lactide) as a biodegradable material for in situ forming implants: evaluation of drug release and in vivo degradation," Drug Development and Industrial Pharmacy, 2015, vol. 41, No. 2, pp. 342-352.
Official Action for European Patent Application No. 16751437.1, dated Jun. 5, 2019 8 pages.

* cited by examiner

*Primary Examiner* — Abigail Vanhorn
(74) *Attorney, Agent, or Firm* — Sheridan Ross P.C.

(57) ABSTRACT

Liquid polymer pharmaceutical compositions with a biodegradable liquid polyester that has a carboxylic acid end group, a biocompatible solvent, and an active pharmaceutical agent are useful for administration into the body to provide extended long term release of the drug.

31 Claims, 9 Drawing Sheets

LIQUID POLYMER DELIVERY SYSTEM FOR EXTENDED ADMINISTRATION OF DRUGS

CROSS REFERENCE TO RELATED APPLICATIONS

This application is a national stage application under 35 U.S.C. 371 of PCT Application No. PCT/US2016/045334, having an international filing date of 3 Aug. 2016, which designated the United States, which PCT claimed the benefit of U.S. Provisional Patent Application 62/200,198, filed 3 Aug. 2015, and U.S. Provisional Patent Application 62/275,407, filed 6 Jan. 2016, the entireties of these which are incorporated herein by reference.

FIELD OF THE INVENTION

This application pertains to the field of biodegradable liquid polymer compositions that may be administered into the body with syringes or needles and that may be utilized to deliver a drug into the body over an extended period of time.

BACKGROUND OF THE INVENTION

Biodegradable polymers are well known for their use in biomedical applications, such as sutures, surgical clips, staples, implants, and drug delivery systems. Such polymers include polyglycolides, polylactides, polycaprolactones, polyanhydrides, polyorthoesters, polydioxanones, polyacetals, polyesteramides, polyamides, polyurethanes, polycarbonates, poly(amino acids), polyphosphazenes, polyketals, polyhydroxybutyrates, polyhydroxyalerates, and polyalkylene oxalates.

Initially, the biodegradable polymers were solid materials that were used to form solid articles such as sutures, staples, surgical clips, implants or microcapsules and microparticles. Because the polymers were solids, all of their applications in the biomedical field required that the polymeric structures be formed outside the body, and then inserted into the body for their use.

U.S. Pat. No. 5,278,201 to Dunn et al. (the "'201 patent") overcame the administration problems with the solid implants by dissolving the solid biodegradable polymers in a biocompatible solvent and injecting the solution into the body using standard syringes and needles where the polymer in the solution precipitates or coagulates upon contact with aqueous body fluid to form a solid implant matrix. The delivery system described in the '201 patent offered a number of advantages, including the ease of manufacture of the polymer solution, the incorporation of the drug into the polymer solution just prior to administration leading to increased drug and polymer stability as well as no loss of drug during the manufacturing process, and the ability to terminally sterilize the polymer solution as well as the drug. However, there remained several disadvantages with this in situ forming polymer system. Because the polymers used were solids with relatively high molecular weights, the polymer solutions formed from the combination of the solid polymers and the biocompatible solvents were quite viscous. Because of the high viscosity, large bore 18-21 gauge needles were required for administration and considerable injection force was needed. In addition, the viscous solutions were not easily injected into muscle tissue and the solid implants formed from these polymer solutions tend to cause local irritation of the muscular tissue. For this reason, the foregoing polymer solutions were normally injected subcutaneously where the material would form quite distinct and noticeable bumps.

U.S. Pat. No. 8,187,640 to Dunn (the "'640 patent") addressed and solved problems associated with the solid implants of the '201 patent. The '640 patent disclosed solution compositions of a biodegradable liquid polymer combined with a biocompatible organic solvent, which solvent would dissipate when the liquid polymer/solvent compositions were placed in a body, thereby forming a viscous liquid polymer material in the form of a film, a coating, a plug or other mass. The viscous liquid polymer material does not solidify upon injection into the body, but rather remains in situ in a viscous liquid form and, when combined with a drug, provides both an initial burst and extended release of the drug.

The '640 patent further disclosed that the rate of release of a drug from the in situ viscous liquid material can be controlled by altering the composition of the biodegradable polymer. The composition of the liquid polymer, i.e., the type of monomer used or the ratio of monomers for copolymers or terpolymers, the end groups on the polymer chains, and the molecular weight of the polymer, determines the hydrophilicity or lipophilicity of the polymer material, as well as the degradation time of the liquid polymer implant. For faster release rates and shorter durations of release, such as over a period of 1 to 3 days, more hydrophilic polymers can be used. On the other hand, for slower release of drug and longer duration of release, such as over a period of 7 to 90 days, more hydrophobic polymer can be used.

The '640 patent does not disclose examples of suitable variations of the end groups of the polymer chains. However, in the Examples section, this patent discloses the use of an alcohol, dodecanol, as an initiator, which results in the insertion of an hydroxy group at the end of the polymer chain.

As described in more detail below, the inventors of the present application have made the low viscosity liquid polymeric delivery system as disclosed in the '640 patent to determine the rate and duration of release of drugs following subcutaneous administration of the drug-loaded delivery system. It was determined that the drug was released in a burst during the initial 24 hours following administration, which was followed by slower release that persisted for 14 days. After 14 days, no significant quantity of drug was released. It was therefore determined that the delivery system of the '640 patent is not suitable for long-term extended delivery of drugs.

SUMMARY OF THE INVENTION

It is one aspect of the present invention to provide a liquid polymer composition for administration into the body of an animal. The liquid polymer composition has a biodegradable liquid polyester with at least one carboxylic acid end group, and a biocompatible organic solvent. A ratio of monomer units to carboxylic acid end groups in the biodegradable liquid polyester is between about 5:1 and about 90:1.

In some embodiments, the biodegradable liquid polyester may be selected from the group consisting of a polylactide, a polyglycolide, a polycaprolactone, a poly(trimethylene carbonate), a polydioxanone, a copolymer thereof, a terpolymer thereof, or any combination thereof.

In some embodiments, the carboxylic acid may be selected from the group consisting of GABA (gamma-amino butyric acid), GHB (gamma-hydroxybutyric acid), lactic acid, glycolic acid, citric acid, and undecylenic acid.

In some embodiments, the biodegradable liquid polyester may have at least about 50% lactide residues.

In some embodiments, the biodegradable liquid polyester may have about 75% lactide residues.

In some embodiments, the biodegradable liquid polyester may have monomer residues selected from the group consisting of caprolactone, trimethylene carbonate and combinations thereof in an amount less than about 50%.

In some embodiments, the biodegradable liquid polyester may have about 25% monomer residues selected from the group consisting of caprolactone, trimethylene carbonate and combinations thereof.

In some embodiments, the biodegradable liquid polyester may be selected from the group consisting of 75:25 lactide:caprolactone and 75:25 lactide:trimethylene carbonate.

In some embodiments, the biodegradable liquid polyester may have an average molecular weight between about 15 kDa and about 30 kDa.

In some embodiments, the biocompatible organic solvent may be at least partially made up of one or more organic solvents selected from the group consisting of amides, acids, alcohols, esters of monobasic acids, ether alcohols, sulfoxides, lactones, polyhydroxy alcohols, esters of polyhydroxy alcohols, ketones, and ethers.

In some embodiments, the biocompatible organic solvent may be at least partially made up of one or more organic solvents selected from the group consisting of N-methyl-2-pyrrolidone (NMP), 2-pyrrolidone, N-ethyl-2-pyrrolidone, N-cycylohexyl-2-pyrrolidone, N-hydroxyethyl-2-pyrrolidone, dimethyl acetamide, dimethyl formamide, acetic acid, lactic acid, ethanol, propanol, methyl lactate, ethyl lactate, methyl acetate, diethylene glycol monomethyl ether, glycofurol, glycerol formal, isopropylidene glycerol, dimethyl sulfoxide, e-caprolactone, butyrolactone, propylene glycol, polyethylene glycol, glycerol, 1,3-butyleneglycol, methoxypolyethylene glycol, methoxypropylene glycol, acetone, methyl ethyl ketone, and tetrahydrofuran.

In some embodiments, the composition may be between about 20 wt % and about 40 wt % biodegradable liquid polyester and between about 40 wt % and about 60 wt % biocompatible organic solvent.

In some embodiments, the animal may be a human.

It is another aspect of the invention to provide a liquid polymer pharmaceutical composition for administration into the body of an animal. The liquid polymer pharmaceutical composition has a biodegradable liquid polyester with at least one carboxylic acid end group, a biocompatible organic solvent, and an active pharmaceutical agent. A ratio of monomer units to carboxylic acid end groups in the biodegradable liquid polyester is between about 5:1 and about 90:1.

In some embodiments, the active pharmaceutical agent may be present in a dosage effective for greater than three days.

In some embodiments, the active pharmaceutical agent may be present in a dosage effective for greater than one week.

In some embodiments, the active pharmaceutical agent may be present in a dosage effective for greater than one month.

In some embodiments, the active pharmaceutical agent may be present in an amount between 0.1% and 60% by weight of the composition.

In some embodiments, the drug may be a hydrophobic small molecule drug. The hydrophobic small molecule drug may be selected from the group consisting of corticosteroids, azole medications, sex steroids, statin drugs, and antiandrogen drugs. The hydrophobic small molecule drug may also be selected from the group consisting of testosterone, prednisone, triamcinolone, prednisolone, beclomethasone, fluticasone, methylprednisone, clobetasol, halobetasol, dexamethasone, metronidazole, fluconazole, ketoconazole, itraconazole, miconazole, dimetridazole, secnidazole, ornidazole, tinidazole, carnidazole, panidazole, estrogens, progestins, including esters thereof, atorvastatin, simvastatin, fluvastatin, lovastatin, pitavastatin, pravastatin, rosuvastatin, abiraterone, galeterone, orteronel, enzalutamide, and salts, esters, complexes, prodrugs, and analogs thereof.

In some embodiments, the drug may be a polymeric drug. The polymeric drug may be selected from the group consisting of degarelix, abaloparatide, leuprolide (leuprorelin), exenatide, liraglutide, albiglutide, dulaglutide, basal insulin, octreotide, goserelin, triptorelin, nafarelin, buserelin, histrelin, deslorelin, ganirelix, abarelix, cetrorelix, teverelix, lanreotide, carfilzomib, human growth hormone, interferon-alpha, interferon-beta, interferon-gamma, interleukin, calcitonin, growth hormone releasing peptides, glucagon-like peptides, granulocyte-colony stimulating factor, nerve growth factor, platelet-derived growth factor, insulin-like growth factor, vascular endothelial growth factor, fibroblast growth factor, bone morphogenic protein, erythropoietin, poly-L-lactic acid (PLLA), and salts, esters, complexes, prodrugs, and analogs thereof. The polymeric drug may also be selected from the group consisting of degarelix, abaloparatide, leuprolide (leuprorelin), exenatide, liraglutide, albiglutide, dulaglutide, basal insulin, octreotide, goserelin, triptorelin, nafarelin, buserelin, histrelin, deslorelin, ganirelix, abarelix, cetrorelix, teverelix, lanreotide, carfilzomib, and salts, esters, complexes, prodrugs, and analogs thereof.

In some embodiments, the biodegradable liquid polyester may be selected from the group consisting of a polylactide, a polyglycolide, a polycaprolactone, a poly(trimethylene carbonate), a copolymer thereof, a terpolymer thereof, or any combination thereof.

In some embodiments, the carboxylic acid may be selected from the group consisting of GABA (gamma-amino butyric acid), GHB (gamma-hydroxybutyric acid), lactic acid, glycolic acid, citric acid, and undecylenic acid.

In some embodiments, the biodegradable liquid polyester may have at least about 50% lactide residues.

In some embodiments, the biodegradable liquid polyester may have about 75% lactide residues.

In some embodiments, the biodegradable liquid polyester may have monomer residues selected from the group consisting of caprolactone, trimethylene carbonate and combinations thereof in an amount less than about 50%.

In some embodiments, the biodegradable liquid polyester may have about 25% monomer residues selected from the group consisting of caprolactone, trimethylene carbonate and combinations thereof.

In some embodiments, the biodegradable liquid polyester may be selected from the group consisting of 75:25 lactide:caprolactone and 75:25 lactide:trimethylene carbonate.

In some embodiments, the biodegradable liquid polyester may have an average molecular weight between about 15 kDa and about 30 kDa.

In some embodiments, the biocompatible organic solvent may be at least partially made up of one or more biocompatible organic solvents that have a water solubility of 10% or higher by weight of the solvent in water.

In some embodiments, the biocompatible organic solvent may be at least partially made up of one or more organic solvents selected from the group consisting of amides, acids, alcohols, esters of monobasic acids, ether alcohols, sulfoxides, lactones, polyhydroxy alcohols, esters of polyhydroxy alcohols, ketones, and ethers.

In some embodiments the biocompatible organic solvent may be at least partially made up of one or more organic solvents selected from the group consisting of N-methyl-2-pyrrolidone (NMP), 2-pyrrolidone, N-ethyl-2-pyrrolidone, N-cycylohexyl-2-pyrrolidone, N-hydroxyethyl-2-pyrrolidone, dimethyl acetamide, dimethyl formamide, acetic acid, lactic acid, ethanol, propanol, methyl lactate, ethyl lactate, methyl acetate, diethylene glycol monomethyl ether, glycofurol, glycerol formal, isopropylidene glycerol, dimethyl sulfoxide, e-caprolactone, butyrolactone, propylene glycol, polyethylene glycol, glycerol, 1,3-butyleneglycol, methoxypolyethylene glycol, methoxypropylene glycol, acetone, methyl ethyl ketone, and tetrahydrofuran.

In some embodiments, the composition may be between about 20 wt % and about 40 wt % biodegradable liquid polyester, between about 40 wt % and about 60 wt % biocompatible organic solvent, and between about 10 wt % and about 30 wt % active pharmaceutical agent.

In some embodiments, the animal may be a human.

It is another aspect of the invention to provide a method of forming a biodegradable, non-solid implant in situ in a body. The method includes the step of injecting a liquid polymer composition into the body. The liquid polymer composition has a biodegradable liquid polyester with at least one carboxylic acid end group, and a biocompatible organic solvent. A ratio of monomer units to carboxylic acid end groups in the biodegradable liquid polyester is between about 5:1 and about 90:1.

It is another aspect of the invention to provide a method of delivering an active pharmaceutical agent to a body. The method includes the step of injecting a liquid polymer pharmaceutical composition into the body. The liquid polymer composition has a biodegradable liquid polyester with at least one carboxylic acid end group, a biocompatible organic solvent, and an active pharmaceutical agent. A ratio of monomer units to carboxylic acid end groups in the biodegradable liquid polyester is between about 5:1 and about 90:1. The active pharmaceutical agent is released within the body for at least three days.

It is another aspect of the invention to provide a liquid polymer pharmaceutical composition for administration into the body of an animal. The liquid polymer pharmaceutical composition has a biodegradable liquid polyester, a biocompatible organic solvent, and an active pharmaceutical agent. The polyester is a poly(DL-lactide-co-caprolactone) with a carboxylic acid end group. The active pharmaceutical agent is selected from the group consisting of testosterone, degarelix, abaloparatide, leuprolide, and pharmaceutically acceptable salts and esters thereof.

In some embodiments, the biodegradable liquid polyester may have at least about 50% lactide residues.

In some embodiments, the biodegradable liquid polyester may have less than about 50% caprolactone residues.

In some embodiments, the biodegradable liquid polyester may be 75:25 lactide:caprolactone.

In some embodiments, the biodegradable liquid polyester may have an average molecular weight between about 15 kDa and about 30 kDa.

In some embodiments, the biodegradable liquid polyester may have an average molecular weight between about 20 kDa and about 25 kDa.

In some embodiments, the biocompatible organic solvent may be at least partially made up of N-methyl-2-pyrrolidone.

In some embodiments, the active pharmaceutical agent may be testosterone undecanoate.

In some embodiments, the active pharmaceutical agent may be selected from the group consisting of degarelix and degarelix acetate.

In some embodiments, the active pharmaceutical agent may be abaloparatide.

In some embodiments, the active pharmaceutical agent may be leuprolide acetate.

In some embodiments, the composition may be between about 20 wt % and about 40 wt % biodegradable liquid polyester, between about 40 wt % and about 60 wt % biocompatible organic solvent, and between about 10 wt % and about 30 wt % active pharmaceutical agent.

In some embodiments, the animal may be a human.

It is another aspect of the invention to provide a delivery system for administration of a liquid polymer pharmaceutical composition. The delivery system has a syringe component, a formulation component with a biodegradable liquid polyester having at least one carboxylic acid end group, and an active pharmaceutical agent. A ratio of monomer units to carboxylic acid end groups in the biodegradable liquid polyester is between about 5:1 and about 90:1. The formulation component and the active pharmaceutical agent are contained within the syringe component.

In some embodiments, the syringe component may be a single syringe containing the formulation component and the active pharmaceutical agent.

In some embodiments, the syringe component may be a two syringe system, with a first syringe containing the formulation component and a second syringe containing the active pharmaceutical agent.

It is another aspect of the invention to provide a liquid polymer composition for administration into the body of an animal or human. The liquid polymer composition has a biodegradable liquid polymer with a carboxylic acid end group, a biocompatible organic solvent, and a therapeutically effective amount of a drug.

It is another aspect of the invention to provide a liquid polymer pharmaceutical composition. The liquid polymer pharmaceutical composition has a biodegradable liquid polyester with at least one carboxylic acid end group, a biocompatible organic solvent, and an active pharmaceutical agent selected from the group consisting of testosterone and pharmaceutically acceptable salts and esters thereof for use in the treatment of androgen deficiency. A ratio of monomer units to carboxylic acid end groups is between about 5:1 and about 90:1.

Figure 2:
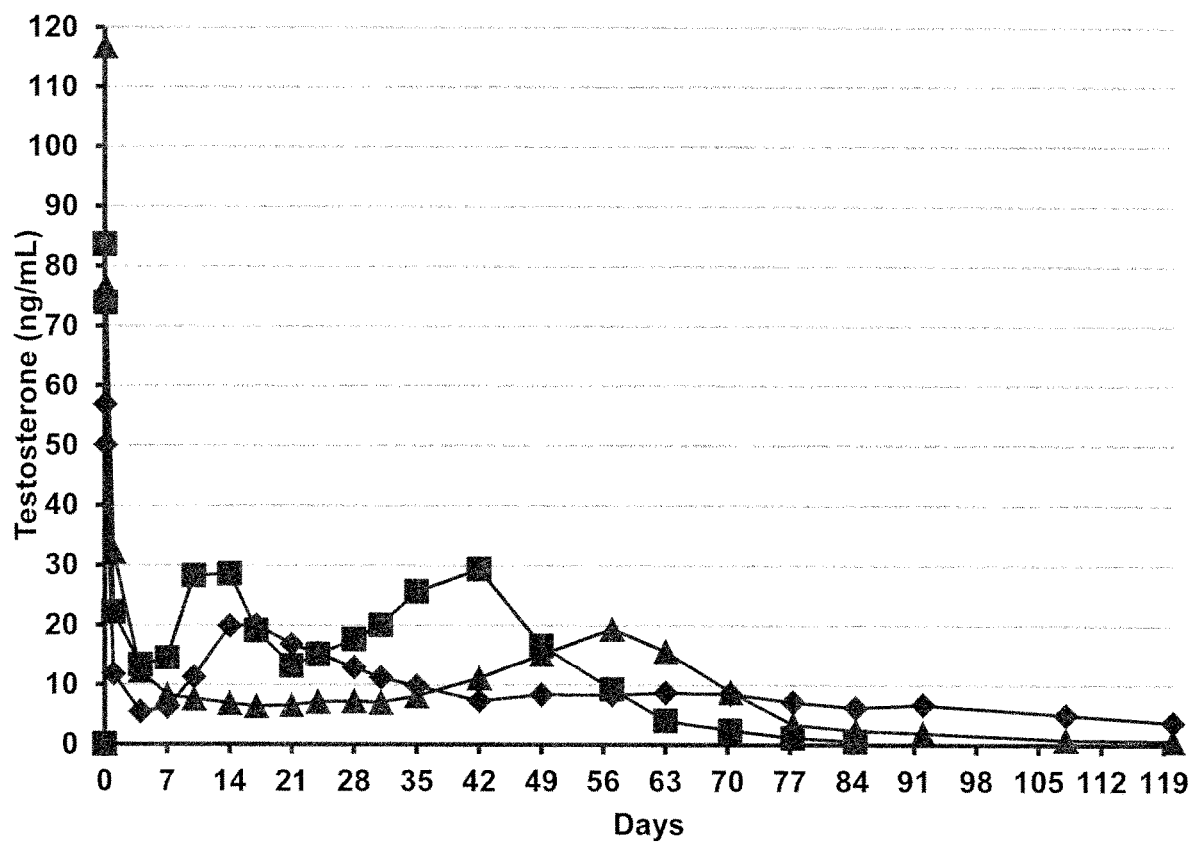

FIG. 2 is a graph showing blood levels of testosterone (ng/ml) over time in rats injected subcutaneously with one of three test compositions containing testosterone, a glycolic acid initiated liquid polymer containing 75% DL-lactide and 25% ε-caprolactone, and a solvent. Symbols: Test Composition A made of 30% the liquid polymer having a molecular weight of 8 kDa, 30% the solvent NMP, and 40% testosterone (■), Test Composition B made of 30% liquid polymer having a molecular weight of 22 kDa, 30% the solvent NMP, and 40% testosterone (♦), Test Composition C made of 30% liquid polymer having a molecular weight of 15 kDa, 30% the solvent combination of 30% NMP and 70% benzyl benzoate, and 40% testosterone (▲).

Figure 3:
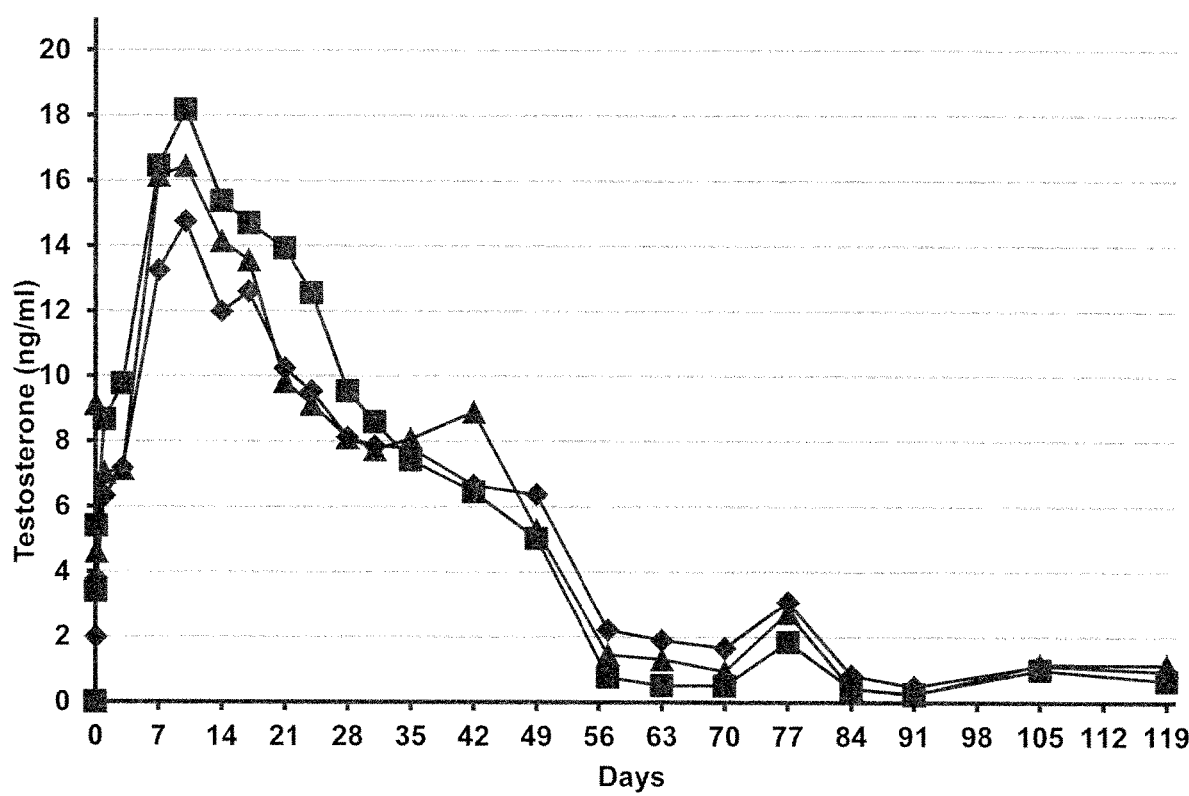

FIG. 3 is a graph showing blood levels of testosterone (ng/ml) over time in rats injected subcutaneously with one of three test compositions containing an ester of testosterone (testosterone cypionate), a glycolic acid initiated liquid polymer containing 75% DL-lactide and 25% ε-caprolactone, and a solvent. Symbols: Test Composition D made of 30% of a liquid polymer having a molecular weight of 22 kDa, 50% the solvent NMP, and 20% testosterone cypionate (■), Test Composition E made of 30% of a liquid polymer having a molecular weight of 25 kDa, 45% the solvent NMP, and 25% testosterone cypionate (♦), Test Composition F made of 30% of a liquid polymer having a molecular weight of 25 kDa, 50% the solvent NMP, and 20% testosterone cypionate (▲).

Figure 4:
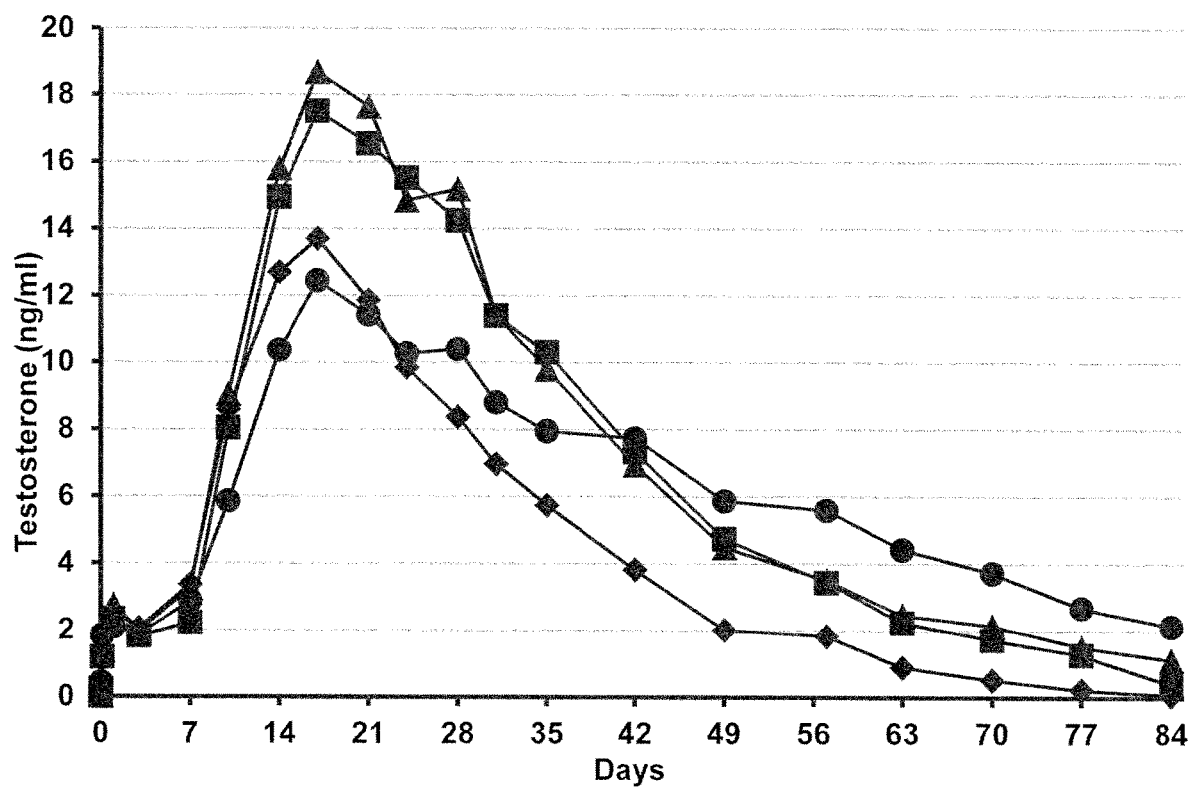

FIG. 4 is a graph showing blood levels of testosterone (ng/ml) over time in rats injected subcutaneously with one of four test compositions containing an ester of testosterone (testosterone undecanoate), a glycolic acid initiated liquid polymer containing 75% DL-lactide and 25% ε-caprolactone, and a solvent. Symbols: Test Composition G made of 20% of a liquid polymer having a molecular weight of 8 kDa, 60% the solvent NMP, and 20% testosterone undecanoate (■), Test Composition H made of 30% of a liquid polymer having a molecular weight of 8 kDa, 50% the solvent NMP, and 20% testosterone undecanoate (♦), Test Composition I made of 20% of a liquid polymer having a molecular weight of 22 kDa, 60% the solvent NMP, and 20% testosterone undecanoate (▲), and Test Composition J made of 30% of a liquid polymer having a molecular weight of 22 kDa, 50% the solvent NMP, and 20% testosterone undecanoate (●).

Figure 5:
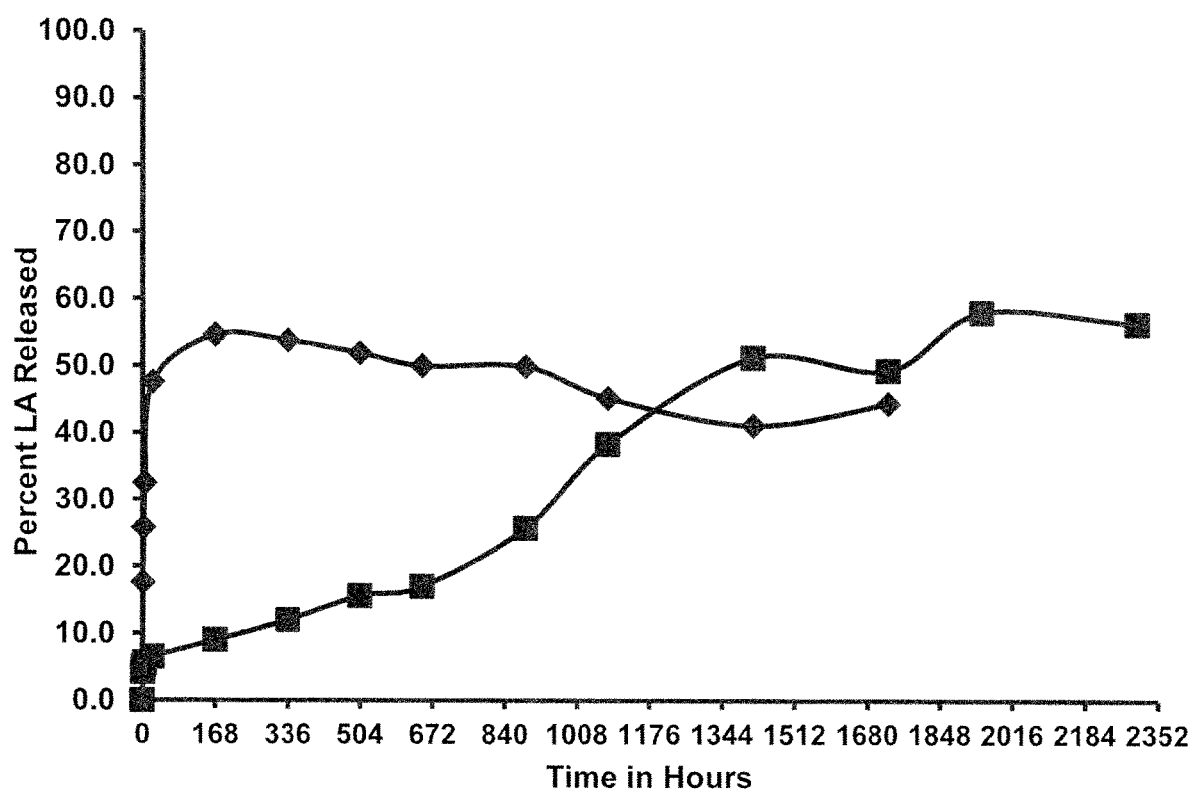

FIG. 5 is a graph comparing release of polymeric drug from a liquid polymer composition in which the liquid polymer is initiated with dodecanol (♦) and from a liquid polymer composition in which the same liquid polymer is initiated with glycolic acid (■).

Figure 6:
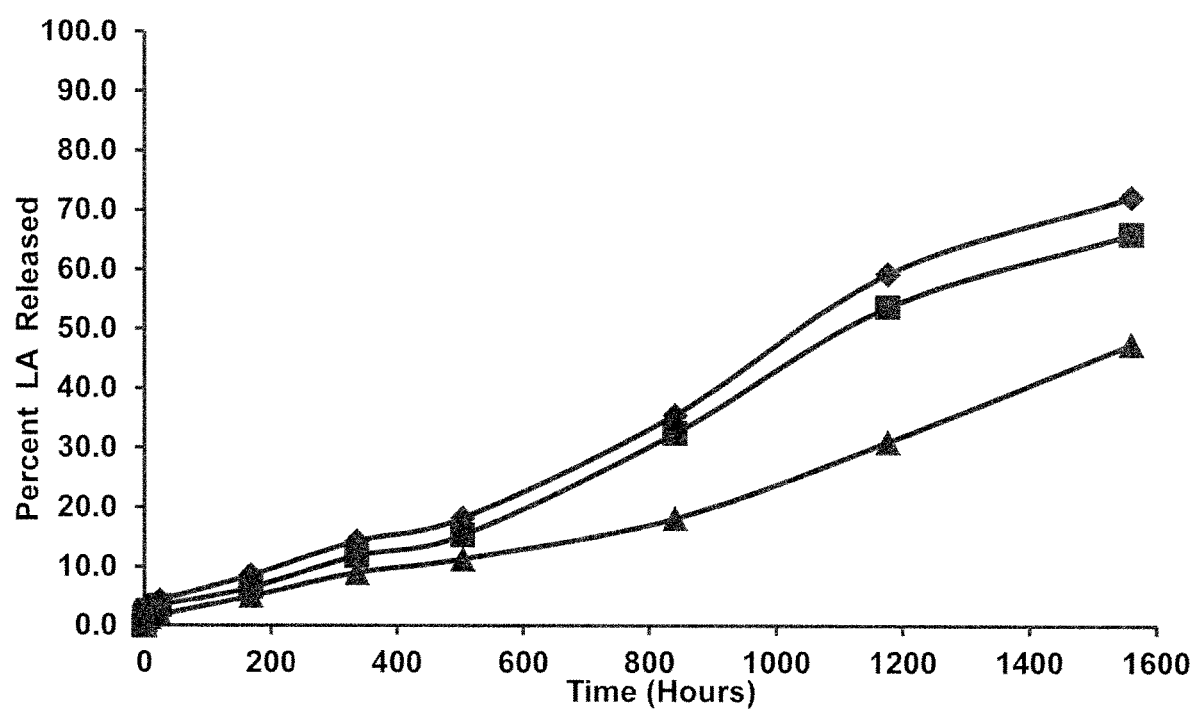

FIG. 6 is a graph showing release of polymeric drug from liquid polymer compositions in which the liquid polymer is initiated with glycolic acid. Symbols: Composition K contained 30% of a liquid polymer having a molecular weight of 14 kDa, 58% the solvent NMP, and 12% leuprolide acetate (♦); Composition L contained 35% of a liquid polymer having a molecular weight of 14 kDa, 53% the solvent NMP, and 12% leuprolide acetate (■); and Composition M contained 40% of a liquid polymer having a molecular weight of 14 kDa, 48% the solvent NMP, and 12% leuprolide acetate (▲).

Figure 7:
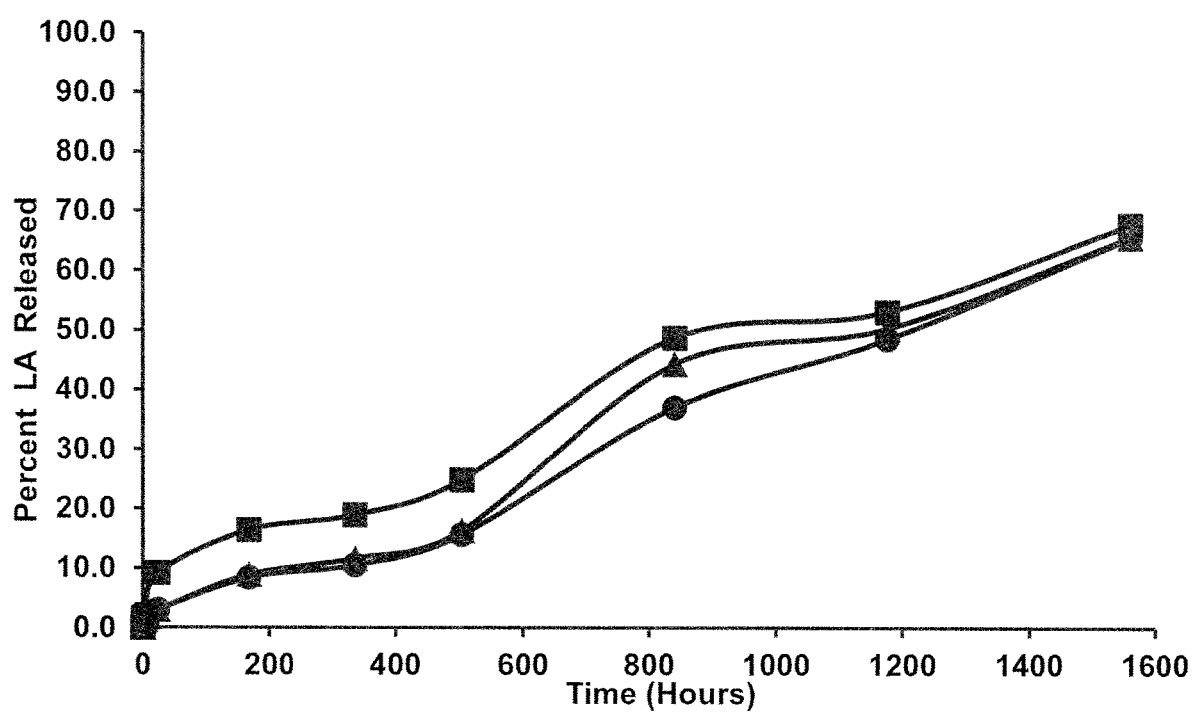

FIG. 7 is a graph showing release of polymeric drug from liquid polymer compositions in which the liquid polymer is initiated with glycolic acid. Composition N contained 30% of a liquid polymer having a molecular weight of 8 kDa, 58% the solvent NMP, and 12% leuprolide acetate (■); Composition O contained 35% of a liquid polymer having a molecular weight of 8 kDa, 53% the solvent NMP, and 12% leuprolide acetate (▲); and Composition P contained 40% of a liquid polymer having a molecular weight of 8 kDa, 48% the solvent NMP, and 12% leuprolide acetate (●).

Figure 8A:
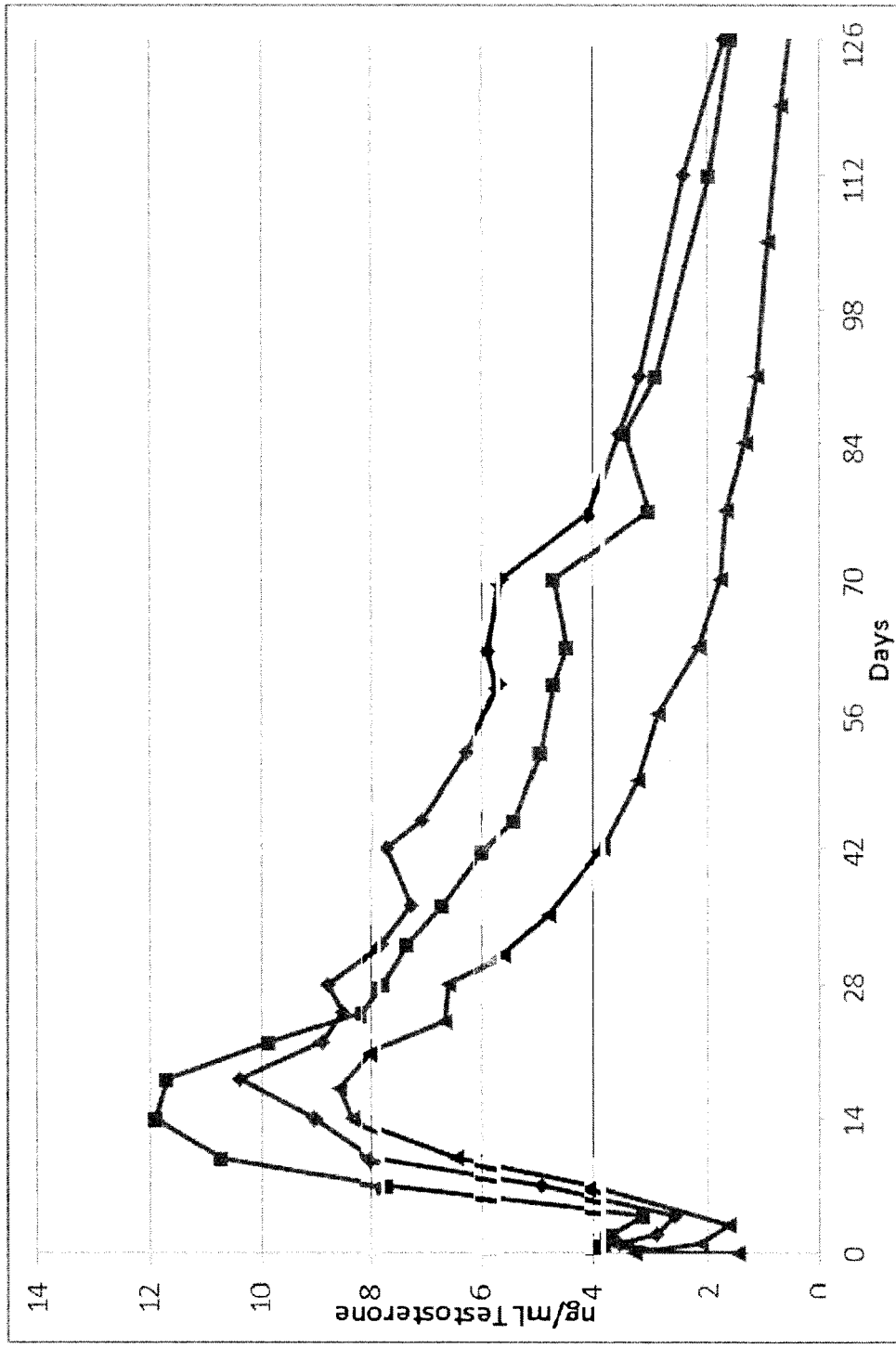
Figure 8B:
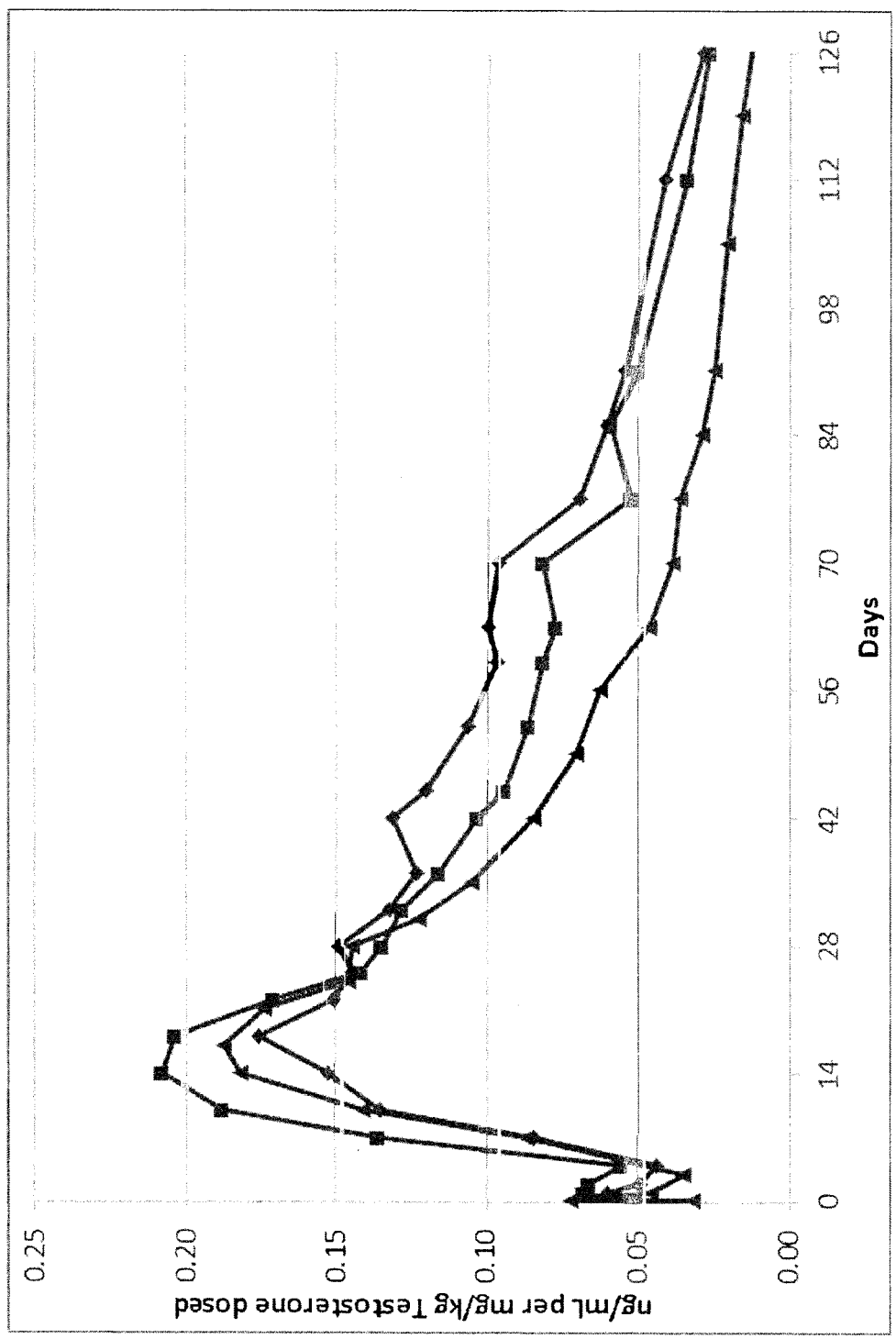

FIGS. 8A and 8B are graphs showing non-normalized and normalized (for dose and body weight) pK data, respectively, showing the release of testosterone over time in rats injected subcutaneously with Compositions Q (■) and R (♦) and a control formulation (▲). Composition Q (■) contained 20% testosterone undecanoate, 30% lactic acid-initiated liquid polymer containing 75% DL-lactide and 25% ε-caprolactone and having a molecular weight of 22 kDa, and 50% NMP. Composition R (♦) contained 20% testosterone undecanoate, 30% glycolic acid-initiated liquid polymer containing 75% DL-lactide and 25% trimethylene carbonate and having a molecular weight of 22 kDa, and 50% NMP. A control formulation (▲) contained 20% testosterone undecanoate, 30% glycolic acid-initiated liquid polymer containing 75% DL-lactide and 25% ε-caprolactone and having a molecular weight of 22 kDa, and 50% NMP.

DETAILED DESCRIPTION OF THE INVENTION

It has been unexpectedly discovered that, in a liquid polymer delivery system that includes a biodegradable liquid polymer combined with a biocompatible organic solvent, such as disclosed in U.S. Pat. No. 8,187,640, the disclosure of which is incorporated herein in its entirety, utilizing a polymer having carboxylic acid end groups as described herein surprisingly provides markedly improved extended release of drugs.

This discovery was especially surprising in view of the fact that the '640 patent discloses that faster release rates and shorter durations of release are obtained with increased hydrophilicity of the liquid polymer. In contrast to what would be expected by a skilled artisan, utilizing a carboxylic acid end group, which is highly hydrophilic, provides a markedly longer duration of release of drugs.

As used herein, the term "animal" refers to any organism of the kingdom Animalia. Examples of "animals" as that term is used herein include, but are not limited to, humans (Homo sapiens); companion animals, such as dogs, cats, and horses; and livestock animals, such as cows, goats, sheep, and pigs.

As used herein, the term "biocompatible" means "not harmful to living tissue."

As used herein, the term "biodegradable" refers to any water-insoluble material that is converted under physiological conditions into one or more water-soluble materials, without regard to any specific degradation mechanism or process.

As used herein, the term "liquid" refers to the ability of a composition to undergo continuous deformation under a shearing stress. Liquid polymer compositions and the liquid polymers according to the invention have a liquid physical state at ambient and body temperatures. The liquid polymer compositions and liquid polymers have a definite volume, but are an amorphous, non-crystalline mass with no definite shape. In addition, the liquid polymers according to the invention are not soluble in body fluid or water and therefore, after injection into the body and dissipation of the solvent, remain as a cohesive mass when injected into the body without themselves significantly dissipating. In addition, such liquid polymer compositions can have a viscosity, density, and flowability to allow delivery of the composition through standard gauge or small gauge needles (e.g., 18-26 gauge) with low to moderate injection force using standard syringes. The liquid polymers of the present invention can be further characterized as not forming a solid implant in situ in the body when injected into the body as part of a sustained release drug delivery system that includes the liquid polymers and a biocompatible solvent. The liquid polymers of the present invention can be further characterized being non-crystalline, amorphous, non-thermoplastic, non-thermosetting, and/or non-solid.

As used herein, the terms "molecular weight" and "average molecular weight," unless otherwise specified, mean a weight-average molecular weight as measured by a conventional gel permeation chromatography (GPC) instrument (such as an Agilent 1260 Infinity Quaternary LC with Agilent G1362A Refractive Index Detector) utilizing polystyrene standards and tetrahydrofuran (THF) as the solvent.

As used herein, the terms "patient" and "subject" are interchangeable and refer generally to an animal to which a composition or formulation of the invention is administered or is to be administered.

As used herein, the term "polymer" refers generally to polymers, copolymers and/or terpolymers that can be linear, branched, grafted and/or star-shaped. Examples of polymers include peptides, polypeptides, proteins, and nucleic acids.

As used herein, the term "small molecule" means an organic compound having a molecular weight less than 900 daltons.

Unless otherwise specified, all ratios between monomers in a copolymer disclosed herein are molar ratios.

The liquid polymer compositions of the invention comprise a biodegradable liquid polyester and a biocompatible organic solvent and are prepared by mixing or blending together the liquid polymer(s) and the organic solvent(s), which can be performed by any method at a temperature ranging from about 10-50° C. (e.g., at about 25° C.) using a suitable device to achieve a homogeneous, flowable liquid at room temperature. Examples of such devices include a mechanical stirrer, a mixer, or a roller mill. Because both the polymer and solvents are liquids, they are readily mixed to form a homogeneous solution or suspension.

Polymers with a carboxylic acid end group, such as a glycolic acid end group, may be made by standard chain-growth polymerization techniques, by combining one or more alkene or alicyclic monomers with a carboxylic acid or water, preferably a hydroxy acid, in the presence of a suitable catalyst, such as tin, for example in the form of stannous octanoate. Carboxylic acids that are suitable are those that contain an alkyl chain, a nucleophile, and are soluble in the monomer used to make the polymer or a combination of the monomer and solvent. Examples of suitable initiators include, but are not limited to, GABA (gamma-amino butyric acid), GHB (gamma-hydroxybutyric acid), lactic acid, glycolic acid, citric acid, and water. Typically, a biodegradable polymer with an acid end group is made by the ring opening polymerization of monomers, such as lactide and/or caprolactone, which is initiated by water or a carboxylic acid compound of the formula Nu-R—COOH where Nu is a nucleophilic moiety, such as an amine or hydroxyl, R is any organic moiety, and the —COOH is a carboxylic acid functionality. The nucleophilic moiety of the molecule acts to initiate the ring opening polymerization in the presence of a catalyst and heat, producing a polymer with a carboxylic acid functionality on one end. A representative polymerization equation is shown below as Formula A.

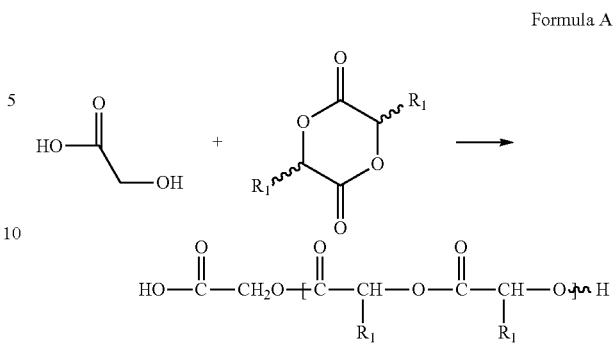

Formula A

Alternatively, a carboxylic acid end group may be created on the end of a polymer chain by post-polymerization modification.

The liquid polymers that can be used according to the present invention are biodegradable, and remain in a liquid (flowable) form at room temperature (e.g., at approximately 25° C.) up to body temperature (e.g., at approximately 37° C.). The characteristic of being liquid is achieved by control of the molecular weight of the polymer and the monomer selection and ratio. In addition, the liquid polymer can have a pre-injection bulk viscosity that allows the composition to be easily administered, and in some embodiments effective to provide a desired controlled release profile of a biologically active agent from the implanted material. Because the liquid polymers are liquid at room temperature, they allow the use of lower concentrations of the biocompatible solvent to be used in the composition to provide a syringeable formulation compared to polymer/solvent compositions prepared with solid polymers.

Examples of suitable liquid polymers that can be used in this application include polylactic acid, polyglycolic acid, polylactide (DL-lactide, D-lactide, L-lactide), polyglycolide, polycaprolactones, polyanhydrides, polyamides, polyurethanes, polyesteramides, polyorthoesters, polydioxanones, polyacetals, polyketals, polycarbonates, polyphosphazenes, polyhydroxybutyrates, polyhydroxyvalerates, polyalkylene oxalates, polyalkylene succinates, poly(malic acid), polyethylene glycol, hyaluronic acid, chitin and chitosan, and copolymers, terpolymers, and combinations or mixtures of the above materials. In one embodiment, the liquid polymer is selected from the group consisting of a polylactide, a polyglycolide, a polycaprolactone, a poly(trimethylene carbonate), a polydioxanone, a copolymer thereof, a terpolymer thereof, or any combination thereof. Preferred materials include those polymers, copolymers or terpolymers made with lactide, glycolide, caprolactone, p-dioxanone, trimethylene carbonate, 1,5-dioxepan-2-one, 1,4-dioxepan-2-one, ethylene oxide, propylene oxide, sebacic anhydride, diketene acetals/diols, and lactic acid with lower molecular weights and amorphous regions to limit crystallinity and subsequent solidification.

Non-limiting examples of suitable liquid polymers according to the invention include copolymers of DL-lactide and ε-caprolactone with molar ratios of lactide/caprolactone ranging from about 75/25 to about 50/50 and optionally with inherent viscosities as determined in a 0.10 g/dL solution of hexafluoroisopropanol (HFIP) at 25° C. from about 0.06 to about 0.38 dL/g, copolymers of caprolactone and 1,4-dioxanone with molar ratios of about 70/30 to about 40/60 and optionally with inherent viscosities of about 0.08 to about 0.24 dL/g, lactide and trimethylene carbonate copolymers such as 75/25 poly(DL-lactide-co-trimethylene carbonate), copolymers of caprolactone and trimethylene carbonate with molar ratios of about 90/10 to about 50/50 and optionally with inherent viscosities of about 0.09 to about 0.25 dL/g, and poly(L-lactic acid) optionally with an inherent viscosity of about 0.06 dL/g, among others. Generally, liquid polymers and liquid polymer compositions of the invention can have an inherent viscosity as determined in a 0.10 g/dL solution of hexafluoroisopropanol at 25° C. from 0.05 to 0.50 dL/g.

In embodiments of the composition, the biodegradable liquid polymer is a copolymer of two monomers having a molar ratio of about 75/25 to about 25/75 with a preferred ratio of about 50/50, and an average molecular weight of between about 5,000 daltons and about 40,000 daltons, preferably between about 15,000 daltons and about 30,000 daltons, and more preferably between about 20,000 and about 25,000 daltons. The molecular weight of the biodegradable liquid polymer may be about 8,000 daltons, about 14,000 daltons, about 15,000 daltons, about 22,000 daltons, or about 25,000 daltons, as exemplified in the Examples below.

Further examples of suitable liquid polymers of the invention include biodegradable liquid polyesters with at least about 50% lactide (including DL-lactide) residues, at least about 55% lactide residues, at least about 60% lactide residues, at least about 65% lactide residues, at least about 70% lactide residues, or at least about 75% lactide residues. Other examples of suitable liquid polymers of the invention include biodegradable liquid polyesters with residues of comonomers selected from caprolactone, trimethylene carbonate and combinations thereof in an amount greater than about 5% and less than about 50%, less than about 45% such residues, less than about 40% such residues, less than about 35% such residues, less than about 30% such residues, or less than about 25% such residues. Further embodiments include liquid polyesters of about 75:25 DL-lactide:ε-caprolactone and of 75:25 DL-lactide:trimethylene carbonate.

The biodegradable liquid polyesters of the invention are also characterized as having at least one carboxylic acid end group. Further, the polyesters can have a ratio of monomer units to carboxylic acid end groups that is between about 5:1 and about 90:1, between about 10:1 and about 90:1, between about 15:1 and about 90:1, between about 20:1 and about 90:1, between about 30:1 and about 80:1, between about 40:1 and about 70:1, between about 50:1 and about 60:1, or about 55:1. Alternatively, the ratio of monomer units to carboxylic acid end groups can be less than about 90:1, less than about 80:1, less than about 70:1, less than about 60:1, or less than about 55:1. The ratio of monomer units to carboxylic acid end groups can range from any whole number ratio to any other whole number ratio within the range of about 5:1 to about 90:1.

The liquid polymers of the invention have a molecular weight suitable for achieving the characteristic of being liquid. In particular, the molecular weight of the polymers can be from about 5,000 daltons to about 40,000 daltons, from about 10,000 daltons to about 35,000 daltons, from about 8,000 daltons to about 25,000 daltons, from about 15,000 daltons to about 30,000 daltons, or from about 20,000 to about 25,000 daltons. The molecular weight of the polymers can also be between about 5,000 daltons and about 11,000 daltons, between about 6,000 daltons and about 10,000 daltons, between about 7,000 daltons and about 9,000 daltons, or about 8,000 daltons. The molecular weight of the biodegradable liquid polymer may be about 8,000 daltons, about 14,000 daltons, about 15,000 daltons, about 22,000 daltons, or about 25,000 daltons, as exemplified in the Examples below. The molecular weight of the polymer can range from any number of daltons to any other number of daltons within the range of about 5,000 daltons to about 40,000 daltons. In addition, the liquid polymers of the invention can have a polydispersity value of from about 1.30 to about 2.50, from about 1.35 to about 2.25, or from about 1.40 to about 2.00.

Solvents that may be used according to the invention are non-toxic and can be either hydrophilic or hydrophobic solvents, or may be a combination of hydrophilic solvents, hydrophobic solvents or hydrophilic and hydrophobic solvents, depending upon the desired release profile and the solubility of the polymer and/or biologically active agent in the polymer/solvent composition. Suitable hydrophilic biocompatible organic solvents that can be used according to the present invention have a water solubility of 10% or higher by weight of the solvent in water. Examples of hydrophilic biocompatible organic solvents include amides such as N-methyl-2-pyrrolidone (NMP), 2-pyrrolidone, N-ethyl-2-pyrrolidone, N-cycylohexyl-2-pyrrolidone, N-hydroxyethyl-2-pyrrolidone, dimethyl acetamide, and dimethyl formamide; acids such as acetic acid and lactic acid; alcohols such as ethanol and propanol; esters of monobasic acids such as methyl lactate, ethyl lactate, and methyl acetate; ether alcohols such as diethylene glycol monomethyl ether, glycofurol, glycerol formal, and isopropylidene glycerol (Solketal); sulfoxides such as dimethyl sulfoxide; lactones such as ε-caprolactone and butyrolactone; polyhydroxy alcohols such as propylene glycol, polyethylene glycol, glycerol, and 1,3-butyleneglycol; esters of polyhydroxy alcohols such as methoxypolyethylene glycol and methoxypropylene glycol; ketones such as acetone and methyl ethyl ketone; and ethers such as tetrahydrofuran.

Suitable hydrophobic biocompatible organic solvents that can be used according to the invention have a water solubility less than 10% by weight of the solvent in water. Examples of hydrophobic biocompatible organic solvents include esters of mono-, di-, and tricarboxylic acids such as ethyl acetate, ethyl butyrate, ethyl oleate, isopropyl palmitate, ethyl palmitate, methyl palmitate, isopropyl myristate, diethyl malonate, diethyl succinate, dimethyl adipate, dimethyl succinate, dibutyl sebacate, triacetin, triethyl citrate, tributyrin, acetyl triethyl citrate, acetyl tributyl citrate, acetyl trihexyl citrate, butyryl trihexyl citrate, and tributyl citrate; esters of caprylic and/or capric acids with glycerol or alkylene glycols such as MIGLYOL 810 or 812 (SASOL GERMANY GMBH) (caprylic/capric triglycerides), MIGLYOL 818 (caprylic/capric/linoleic triglyceride), MIGLYOL 829 (caprylic/capric/succinic triglyceride), and MIGLYOL 840 (propylene glycol dicaprylate/caprate); aromatic alcohols such as benzyl alcohol; esters of aromatic acids such as ethyl benzoate and benzyl benzoate; esters of carbonic acid such as propylene carbonate and dimethyl carbonate; amides such as N,N-diethyl-toluamide, N-dodecyl-2-pyrrolidone, N-octyl-2-pyrrolidone, N-methyl-2-caprolactam, and N-dodecyl-caprolactam; fatty acids such as heptanoic acid and oleic acid; and oils such as sesame oil, peanut oil, and castor oil.

The organic solvent is typically added to the compositions in an amount ranging from about 10 percent to about 70 percent by weight, from about 15 percent to about 65 percent by weight, from about 20 percent to about 60 percent by weight, from about 25 percent to about 55 percent by weight, from about 25 percent to about 50 percent by weight, from about 25 percent to about 45 percent by weight, from about 25 percent to about 40 percent by weight, or from about 25 percent to about 35 percent by weight, relative to the total weight of the composition. In other embodiments, the amount of solvent in compositions of the invention can range from any whole number percent to any other whole number percent within the range of from about 10 percent to about 70 percent by weight. The concentration of solvent allows for the level of liquid polymer in the compositions to range from about 10 percent to about 90 percent by weight, from about 15 percent to about 85 percent by weight, from about 20 percent to about 80 percent by weight, from about 25 percent to about 75 percent by weight, from about 30 percent to about 70 percent by weight, from about 35 percent to about 65 percent by weight, from about 40 percent to about 60 percent by weight, from about 45 percent to about 55 percent by weight relative to the overall composition. In other embodiments, the amount of liquid polymer in compositions of the invention can range from any whole number percent to any other whole number percent within the range of from about 10 percent to about 90 percent by weight. In one embodiment, the liquid polymer composition comprises between about 20 wt % and about 40 wt % biodegradable liquid polyester, between about 40 wt % and about 60 wt % biocompatible organic solvent, and optionally between about 10 wt % and about 30 wt % active pharmaceutical agent. The liquid polymer/solvent concentrations permit the liquid polymer/solvent compositions to be easily injected with standard syringes and small gauge needles (e.g., about 18-26 gauge). The compositions of the invention can be administered into the body of a human subject or other animal such as a dog, cat, horse, cow, goat, sheep, or pig.

The liquid polymer and organic solvent composition with an active pharmaceutical agent can be applied or injected into the body of a subject or onto an object (e.g., mesh, catheter, a screw, plate, tack, pin, staple, sponge, etc.) using a device such as a syringe or needle. A device with the composition thereon can be placed into the body of the subject. Suitable routes of injection include, but are not limited to, any parenteral route, such as subcutaneous, intramuscular, and intradermal routes. Other routes of administration include, but are not limited to, topical administration, or sublingual administration (such as on a film or similar system). Following injection or use, the organic solvent dissipates to leave a liquid bolus of polymer and active pharmaceutical agent. The liquid polymer component of the implanted polymer/solvent compositions of the invention will flow and fill the voids left by the organic solvent as it dissipates from the implanted material. The implanted liquid polymer material remains as a liquid with a fluctuant (flowable) consistency so that it remains movable and compressible and gradually biodegrades in the subject's body over time. Because the liquid polymer is not soluble in body fluid or water, the bolus within the body tissue does not dissipate by dissolution in body fluid, but remains as a cohesive mass.

The liquid polymer/solvent compositions can be used as controlled release compositions to provide a delivery system in which a drug or other biologically active agent is added to the liquid polymer/solvent composition to form a liquid polymer pharmaceutical composition prior to injection or other route of administration to the body. Upon exposure to body fluid, the organic solvent dissolves or dissipates in the aqueous tissue fluid to leave the more viscous liquid polymer for release of the encapsulated or entrapped active agent. The liquid polymer implant formed from compositions of the present invention by the dissolution or dissipation of the solvent can be used to control the release of biologically active agents with low initial burst and extended release of the drug.

Liquid polymer pharmaceutical compositions of the invention have been found to release drugs in a patient over a surprisingly long period of time, release a surprisingly high total amount of drug and allow for modulation of initial burst profiles to achieve a high or low initial burst, as desired. In various embodiments, an active pharmaceutical agent in a liquid polymer pharmaceutical composition of the invention is released in a patient, for example as determined by measuring blood serum levels of the agent in a patient, for greater than three days, greater than one week, greater than two weeks, greater than three weeks, greater than four weeks, greater than one month, greater than two months, greater than three months, greater than four months, greater than five months, greater than six months, greater than nine months, or greater than one year. Such levels of agent can be at levels having a pharmacologic or therapeutic effect.

An embodiment of the present invention is a method to treat, provide a therapy for, cure, or prevent a disease, disorder, or other ailment by administration of a liquid polymer pharmaceutical composition comprising an active pharmaceutical agent, as described in detail elsewhere herein. These methods can be used to treat, provide a therapy for, cure, or prevent microbial infections or any other infections by a pathogen, autoimmune disorders, allergies, inflammations, cancers, endocrine disorders, metabolic disorders, neurological disorders, psychological disorders, cardiovascular disorders, or any other diseases, disorders, or other ailments treated by the active pharmaceutical agents described herein.

Active pharmaceutical agents (e.g., drugs) that are suitable for the present application are biologically active agents that provide a biological effect and that act locally or systemically in the treatment, therapy, cure and/or prevention of a disease, disorder, or other ailment. Examples of drugs include, without limitation, antimicrobials, anti-infectives, anti-parasitic drugs such as avermectins, antigens, anti-allergenics, steroidal anti-inflammatory agents, non-steroidal anti-inflammatory agents, anti-tumor agents, anticancer drugs, decongestants, miotics, anti-cholinergics, sympathomimetics, sedatives, hypnotics, psychic energizers, tranquilizers, endocrine/metabolic agents, hormones, GLP-1 agonists, androgenic steroids, estrogens, progestational agents, LHRH agonists and antagonists, somatotropins, narcotic antagonists, humoral agents, prostaglandins, analgesics, antispasmodics, antimalarials, antihistamines, cardioactive agents, antiparkinsonian agents, antihypertensive agents, vaccines, anti-virals, antipsychotics, immunosuppressants, anesthetics, antifungals, antiproliferatives, anticoagulants, antipyretics, antispasmodics, growth factors, cell adhesion factors, cytokines, biological response modifiers, and nutritional agents.

The drug may be, for example, a small molecule organic compound or a polymer, such as a peptide, polypeptide, protein, DNA, or RNA material. The small molecule drug may be a hydrophobic drug, such as corticosteroids such as prednisone, prednisolone, beclomethasone, fluticasone, methylprednisone, triamcinolone, clobetasol, halobetasol, and dexamethasone; azole medications such as metronidazole, fluconazole, ketoconazole, itraconazole, miconazole, dimetridazole, secnidazole, ornidazole, tinidazole, carnidazole, and panidazole; sex steroids such as testosterone, estrogens such as estradiol, and progestins, including esters thereof; statin drugs such as atorvastatin, simvastatin, fluvastatin, lovastatin, pitavastatin, pravastatin, and rosuvastatin; and antiandrogen drugs such as abiraterone, galeterone, orteronel, and enzalutamide and salts, esters, complexes, prodrugs and analogs of the foregoing.

Examples of peptide and polymeric drugs that are suitable for the present application include degarelix, abaloparatide, leuprolide (leuprorelin), exenatide, liraglutide, albiglutide, dulaglutide, basal insulin, octreotide, goserelin, triptorelin, nafarelin, buserelin, histrelin, deslorelin, ganirelix, abarelix, cetrorelix, teverelix, lanreotide, carfilzomib, human growth hormone, interferon-alpha, interferon-beta, interferon-gamma, interleukin, calcitonin, growth hormone releasing peptides, glucagon-like peptides, granulocyte-colony stimulating factor, nerve growth factor, platelet-derived growth factor, insulin-like growth factor, vascular endothelial growth factor, fibroblast growth factor, bone morphogenic protein, erythropoietin, poly-L-lactic acid (PLLA), and salts, complexes, prodrugs, and analogs thereof.

Examples of specific additional drugs that may be utilized include hydrophilic and hydrophobic small molecule drugs such as rivastigmine tartrate, cisplatin, carboplatin, paclitaxel, rapamycin, tacrolimus (fujimycin), bortezomib, trametinib, methotrexate, riociguat, macitentan, sumatriptan, anastozole, fulvestrant, exemestane, misoprostol, follicle-stimulating hormone, axitinib, paricalcitol, pomalidomide, dustasteride, doxycycline, doxorubicin, ciprofloxacin, quinolone, ivermectin, eprinomectin, doramectin, leflunomide, teriflunomide, haloperidol, diazepam, risperidone, olanzapine, amisulpride, aripiprazole, asenapine, clopazine, iloperidone, lurasidone, paliperidone, quetiapine, ziprasidone, bupivacaine, lidocaine, ropivacaine, naltrexone, fentanyl, buprenorphine, butorphanol, loperamide, afamelanotide (melanotan I), melanotan II, fingolimod, and salts, complexes, prodrugs, and analogs thereof.

One suitable drug that may be utilized in the present invention is testosterone or an ester thereof, including but not limited to testosterone undecanoate, also known as testosterone undecylate. Testosterone undecanoate is an ester of the hormone testosterone used in androgen replacement therapy, primarily for the treatment of male hypogonadism. Testosterone undecanoate may also be used as a male contraceptive. As previously known and described in the art, testosterone undecanoate may be administered to males over 18 years of age as an initial 750 mg, 3 mL intramuscular dose, followed by another 750 mg, 3 mL intramuscular dose after four weeks and further 750 mg, 3 mL intramuscular doses every ten weeks thereafter. Further embodiments of the invention include liquid polymer pharmaceutical compositions of testosterone or testosterone undecanoate and use thereof in the treatment of androgen deficiency, in particular male hypogonadism, by administration to a subject having androgen deficiency, such as a male having hypogonadism in amounts and dosing schedules described above and by routes of administration as disclosed elsewhere herein.

Another suitable drug that may be utilized in the present invention is the hormone degarelix or an ester thereof, such as degarelix acetate. Degarelix and esters thereof may be used in hormonal treatment of prostate cancer. As previously known and described in the art, degarelix may be administered to patients with hormone-dependent advanced prostate carcinoma as an initial set of two 120 mg (i.e., totaling 240 mg) subcutaneous doses, followed by an 80 mg subcutaneous dose every 28 days thereafter. Further embodiments of the invention include liquid polymer pharmaceutical compositions of degarelix or esters thereof and use thereof in the treatment of cancer (including prostate and breast cancer), endometriosis, uterine fibroids, or central precocious puberty (CPP), by administration to a patient in need thereof in amounts and dosing schedules described above and by routes of administration as disclosed elsewhere herein. For example, liquid polymer compositions containing degarelix can be used to treat prostate cancer by administration to a male having hormone-dependent advanced prostate carcinoma.

Another suitable drug that may be utilized in the present invention is abaloparatide. Abaloparatide is a parathyroid hormone-related protein (PTHrP) analog drug that has attracted interest as a potential treatment for osteoporosis. Like the related drug teriparatide, but unlike bisphosphonates, abaloparatide is an anabolic (i.e., bone-growing) agent. As previously known and described in the art, transdermal and subcutaneously injectable formulations of abaloparatide are currently in clinical development. Further embodiments of the invention include liquid polymer pharmaceutical compositions of abaloparatide and use thereof in the treatment of osteoporosis by administration to a patient having osteoporosis in amounts and dosing schedules and by routes of administration as disclosed elsewhere herein.

Another suitable drug that may be utilized in the present invention is leuprolide acetate, a salt of the gonadotropin-releasing hormone analog (also known as a luteinizing hormone-releasing hormone (LHRH) agonist) leuprolide (also known as leuprorelin). Leuprolide acetate has found uses in the treatment of various forms of cancer, particularly prostate and breast cancers, as well as endometriosis, uterine fibroids, and (CPP). As previously known and described in the art, treatment of advanced prostate cancer with leuprolide acetate may consist of 7.5 mg intramuscular doses administered monthly, 22.5 mg intramuscular doses administered every three months, 30 mg intramuscular doses administered every four months, or 45 mg intramuscular doses administered every six months. As previously known and described in the art, treatment of endometriosis with leuprolide acetate may consist of 3.75 mg intramuscular doses administered monthly for up to six months, or two 11.25 mg doses administered at three-month intervals. As previously known and described in the art, treatment of uterine fibroids with leuprolide acetate may consist of 3.75 mg intramuscular doses administered monthly for up to three months, or a single 11.25 mg intramuscular dose. Further embodiments of the invention include liquid polymer pharmaceutical compositions of leuprolide or esters thereof and use thereof in the treatment of cancer (including prostate and breast cancer), endometriosis, uterine fibroids, or CPP by administration to a patient in need thereof in amounts and dosing schedules described above and by routes of administration as disclosed elsewhere herein.

The concentration of active pharmaceutical agent in compositions of the invention depends on the drug that is included in the composition and may range from 0.1% to 60% by weight of the composition or higher. Typically, the concentration of agent in the composition is between 10% and 50% by weight of the composition, such as between 20% and 40% by weight of the composition. In other embodiments, the amount of active pharmaceutical agent in compositions of the invention can range from any whole number percent to any other whole number percent within the range of from about 1 percent to about 60 percent by weight.

Because a beneficial characteristic of the compositions disclosed herein is improved extended release of an active pharmaceutical agent, the amount of active pharmaceutical agent will be suitable for long term treatment with the agent in accordance with the time frames disclosed herein. Other embodiments of the invention include single dosage formulations of the liquid polymer pharmaceutical composition which include the liquid polymer composition as described herein with an amount of an active pharmaceutical agent suitable for extended release. For example, such single dosage formulations can include sufficient active pharmaceutical agent for treatment of a patient for greater than three days, greater than one week, greater than two weeks, greater than three weeks, greater than four weeks, greater than one month, greater than two months, greater than three months, greater than four months, greater than five months, greater than six months, greater than nine months, or greater than one year. Compositions may be administered repeatedly as needed (e.g. every month, every three months, every six months, etc.).

The active pharmaceutical agent may be in the form of a liquid or a finely divided solid that is either dissolved or dispersed in the liquid polymer/solvent composition. The agent is incorporated into the composition in an amount sufficient to achieve the desired therapeutic effect, the desired release profile, and the desired period of release. There is no critical upper limit on the amount of the agent that is dispersed or dissolved in the liquid polymer/solvent solution as long as the solution has a fluid viscosity acceptable for injection through a standard or small gauge syringe needle (e.g., gauge of 18-26). The lower limit of the amount of the agent incorporated into the liquid polymer/solvent solution is dependent upon the activity of the agent, the release rate needed to achieve the desired therapeutic level, and the length of time for treatment. Both soluble and insoluble active pharmaceutical agents may be incorporated into the liquid polymer/solvent system.

Liquid polymer/solvent compositions comprising an active pharmaceutical agent according to the present invention may appropriately be either a "solution" or a "suspension" of the active pharmaceutical agent in the solvent. Particularly, it is to be understood that although liquid polymer is dissolved in the solvent, the active pharmaceutical agent may either be dissolved in the solvent (as in a solution), or form solid particles sufficiently large for suspension and sedimentation as part of a heterogeneous mixture (as in a suspension).

The compositions may include various adjuvants or additives, such as colorants, diluents, carriers, excipients, and stabilizers.

A further embodiment of the invention is a delivery system for administration of a liquid polymer pharmaceutical composition to an animal that includes a syringe component, a formulation component and an active pharmaceutical agent. The formulation component includes a biodegradable liquid polyester comprising at least one carboxylic acid end group, with a ratio of monomer units to carboxylic acid end groups between about 5:1 and about 90:1 and a biocompatible organic solvent. In this embodiment, the formulation component and the active pharmaceutical agent are contained within the syringe component. The syringe component can be a single syringe containing the formulation component and active pharmaceutical agent, including without limitation, a mixing syringe or dual-chambered syringe configured to mix compositions contained within each chamber (e.g., a formulation component and an active pharmaceutical agent) prior to administration to a subject. Alternatively, the syringe component can be a two syringe system wherein a first syringe of the two syringe system contains the formulation component and a second syringe of the two syringe system contains the active pharmaceutical agent. In this embodiment, prior to administration, the first and second syringes cooperate to allow mixture of the formulation component and the active pharmaceutical agent which can then be administered to a patient by injection.

Other embodiments of the invention include liquid polymer pharmaceutical compositions as described herein, including for example, wherein the active pharmaceutical agent is selected from the group of testosterone, degarelix, abaloparatide, leuprolide and pharmaceutically acceptable salts and esters thereof, for use in the treatment of conditions disclosed herein as being treatable by the active pharmaceutical agent in the composition.

Liquid polymer pharmaceutical compositions suitable for use in the present invention may be terminally sterilized for administration to an animal, and in particular for administration to a human. Terminal sterilization may be accomplished, by way of non-limiting example, by electron beam sterilization, or by other methods known to those skilled in the art.

The inventors have discovered that the rate of release of a drug from a composition containing a liquid polymer delivery system that includes a biodegradable liquid polymer that has a carboxylic acid end group in combination with a biocompatible organic solvent provides markedly improved extended release of drugs following administration of the delivery system into the body of an animal. As described below in the Examples, the duration of release is markedly extended beyond that which is obtained when utilizing a similar liquid polymer delivery system that differs in the identity of the initiator end group of the biodegradable liquid polymer.

The invention is illustrated by the following non-limiting examples.

Example 1: Prior Art Test Compositions

A 50/50 DL-Lactide/Caprolactone liquid polymer was made as disclosed in Example 1 of U.S. Pat. No. 8,187,640. The polymer was made using dodecanol as an initiator. This polymer was combined with the solvent N-methyl-2-pyrrolidone (NMP) (see, e.g., Example 3, 4 or 5 of the '640 patent), in equal concentrations to provide a drug-free composition that was used as a control in the subsequent study.

Five different test compositions were made substantially as described above and using testosterone as the test drug. The first four test compositions (Test Compositions 1 to 4, respectively) varied from each other in the ratios of liquid polymer, solvent, and drug. Test Composition 1 contained 40% testosterone, 35% of the liquid polymer, and 25% of the NMP solvent. Composition 2 contained 20% testosterone, 40% of the liquid polymer, and 40% of the NMP solvent. Composition 3 contained 40% testosterone, 35% of the liquid polymer, and 25% of the NMP solvent. Composition 4 contained 20% testosterone, 40% of the liquid polymer, and 40% of the NMP solvent. Test Composition 5 differed in the composition of the liquid polymer. Whereas the control composition and the test compositions 1 to 4 utilized a liquid polymer that was 50% DL-lactide and 50% ε-caprolactone, Test Composition 5 contained a liquid polymer that was 75% DL-lactide and 25% ε-caprolactone, initiated with dodecanol. Test Composition 5 contained 40% Testosterone, 40% of the liquid polymer, and 20% of the NMP solvent.

Example 2: Release Profiles from Prior Art Compositions

Castrated male rats were divided into 6 groups, which were tested with the control composition and Test Compositions 1 to 5, as described in Example 1. More specifically, each rat received a subcutaneous injection of 100 mg/kg testosterone equivalent of the appropriate composition; control animals received approximately 10 mg of appropriate composition. Serum levels of testosterone were measured at intervals over a period of 70 days. Results are shown in FIG. 1.

Figure 1:
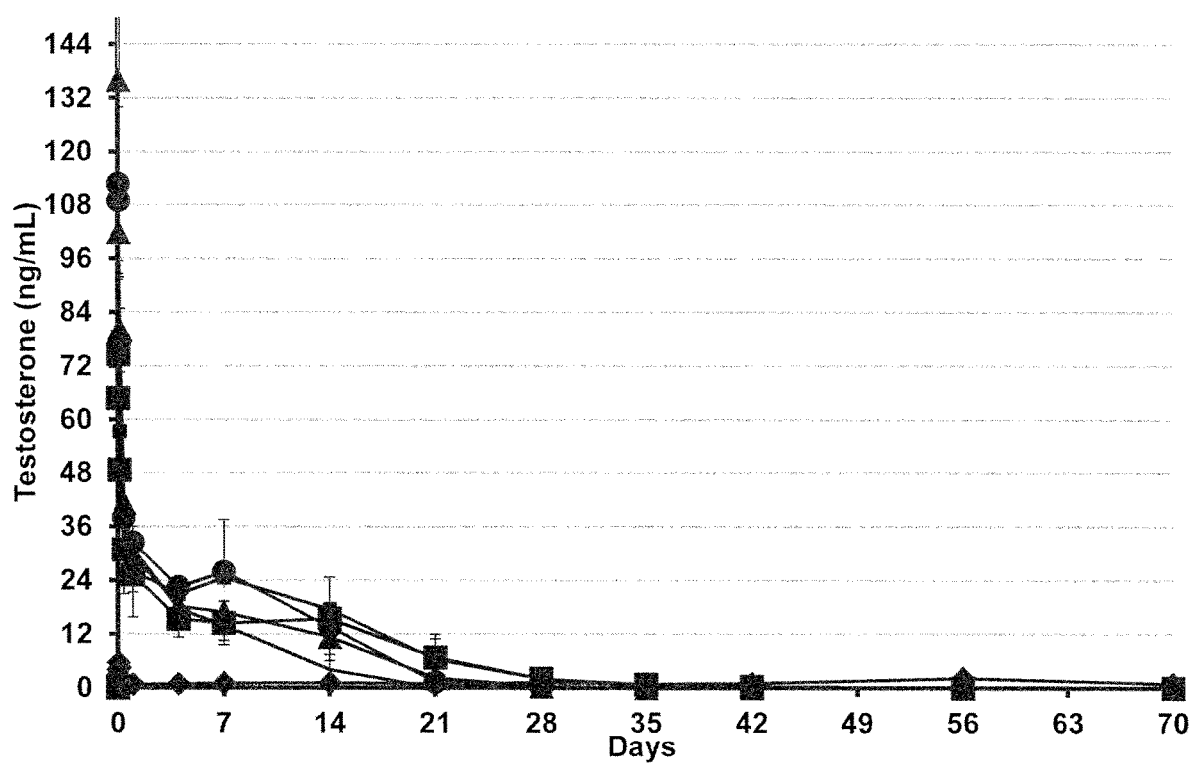
FIG. 1 is a graph showing blood levels of testosterone (ng/ml) over time in rats injected subcutaneously with a prior art liquid polymer delivery system containing a 50% DL-lactide and 50% ε-caprolactone initiated with dodecanol and a solvent (N-methyl-2-pyrrolidone (NMP)), combined with testosterone. Symbols: Control composition of the liquid polymer delivery system and lacking testosterone (♦), Test Composition 1 made of 35% the prior art liquid polymer, 25% the solvent, and 40% testosterone (■), Test Composition 2 made of 40% the prior art liquid polymer, 40% the solvent, and 20% testosterone (▲), Test Composition 3 made of 35% the prior art liquid polymer, 25% the solvent, and 40% testosterone (×), Test Composition 4 made of 40% the prior art liquid polymer, 40% the solvent, and 20% testosterone (−), and Test Composition 5 made of 40% of a prior art liquid polymer (75% DL-lactide and 25% ε-caprolactone), 20% the solvent, and 40% testosterone (●).

As shown in FIG. 1, no serum level of testosterone was detectable in rats that received the control composition containing polymer and solvent but lacking testosterone (FIG. 1 (♦)). Testosterone levels for each of the 5 test compositions were similar throughout the study (FIG. 1: Test Composition 1 (■), Test Composition 2 (▲), Test Composition 3 (×), Test Composition 4 (−), and Test Composition 5 (●)). Each of the test groups showed an initial burst release spike in testosterone level shortly after injection, and after 14 days, the quantity of drug released declined rapidly until day 21, with essentially no testosterone being detected by day 30.

Example 3: Compositions of the Invention Containing Testosterone

75/25 DL-lactide/caprolactone liquid polymers (75% DL-lactide and 25% ε-caprolactone) were made using methods substantially similar to those disclosed in Example 1 of U.S. Pat. No. 8,187,640 except that, in place of dodecanol, glycolic acid was used as a polymer initiator, which results in polymers having carboxylic acid end groups that were not disclosed in the '640 patent. These polymers were combined with a solvent (NMP) in equal concentrations to provide a drug-free polymer/solvent composition.

Briefly, to produce liquid polymers of the invention described in this Example 3, and/or as described in the subsequent Examples below, having a target weight average molecular weight of 8 kDa, 15 kDa, 22 kDa, or 25 kDa, the following process was used.

A 500 mL 2-part glass reactor equipped with a nitrogen inlet, an overhead stirrer with a vacuum-capable stir guide and a vacuum outlet leading to a vacuum trap and vacuum pump was assembled and placed in an oil bath. The oil bath was set at 100° C. and the reactor was placed under vacuum to remove any residual moisture.

To produce a liquid polymer with a target weight average molecular weight of 8 kDa, 316.46 gm (2.20 mol) of DL-lactide, 83.54 gm (0.73 mol) of ε-caprolactone and 11.6 gm (0.1525 mol) of glycolic acid were weighed out. To produce a liquid polymer with a target average molecular weight of 15 kDa, 395.6 gm (2.7 mol) of DL-lactide, 52.2 gm (0.91 mol) of ε-caprolactone and 5.1 gm (0.07 mol) of glycolic acid were weighed out. To produce a liquid polymer with an average molecular weight of 15 kDa, 316.8 g (2.2 mol) of DL-lactide, 83.4 g (0.73 mol) of ε-caprolactone and 5.8 g (0.08 mol) of glycolic acid were weighed out. To produce a liquid polymer with an average molecular weight of 25 kDa, 395.3 g (2.7 mol) of DL-lactide, 104.5 g (0.91 mol) of ε-caprolactone, and 4.0 g (0.05 mol) of glycolic acid were weighed out. It is noted that the quantities of polymer and initiator shown in this Example are illustrative and that the exact quantities of polymer and initiator may vary slightly when different lots of polymer are used. The calculations used to achieve a desired or target average molecular weight are within the ability of one skilled in the art.

For each polymer composition, the vacuum on the reactor was broken with nitrogen and the reactor charged with DL-lactide, glycolic acid and ε-caprolactone via a glass funnel. The stirrer was turned to 10-50 rpm, the oil bath set to 160° C., and the system vacuum purged and back flushed with nitrogen three times. The reactor was then left under a slight nitrogen purge.

A catalyst solution was prepared by weighing ca. 0.3 gm of tin(II) 2-ethylhexanaote (stannous octoate) into a 10 mL volumetric flask and diluting to the mark with anhydrous toluene. For the 8 kDa polymer, the amount needed to add 0.03 wt % stannous octoate based on monomer weight was calculated as 0.12 g (4 mL) to inject. For the 15 kDa and 22 kDa polymers, the amount needed to add 0.03 wt % stannous octoate based on monomer weight was calculated as 0.15 g (5 mL) to inject. The catalyst calculations used to achieve a desired or target average molecular weight are within the ability of one skilled in the art.

For all polymer compositions described in this and subsequent Examples, once the monomers had melted and the oil bath reached 160° C., the catalyst was injected via a syringe equipped with a 6-inch blunt tipped 20 g needle with stirring. The polymerization reaction was continued for 16-18 hours. After the appropriate reaction time the vacuum trap was immersed in an ice bath and the nitrogen inlet closed. Vacuum was applied slowly to the stirred reaction mix for 4-6 hours with an ultimate vacuum of −22 to −25 in. Hg. Unreacted monomer was collected in the vacuum trap. After the appropriate time the vacuum was discontinued, the reactor purged with nitrogen, removed from the oil bath and the liquid polymer poured into a glass or PYREX® (low-thermal-expansion plastic borosilicate glass) container and cooled. Yield was approximately 85% for all polymer compositions.

Weight average molecular weight of the polymers was determined by gas permeation chromatography (GPC) with a refractive index detector (e.g., Agilent 1260 Infinity Quaternary LC with Agilent G1362A Refractive Index Detector).

To produce various formulations of the invention using polymer, solvent and drug, the following procedure was generally used. Polymer produced as discussed above was weighed into a polypropylene jar and N-methyl-2-pyrrolidone (NMP) (or in Composition C below, the indicated mixture of NMP and benzyl benzoate) was added to the liquid polymer. The mixture was heated in an oven to assist in the dissolution and/or dispersion of the NMP in the polymer. Complete homogeneous dissolution required mixing with SPEEDMIXER™ (i.e., a high-speed mixer; Flack-Tek, Landrum, S.C.) or a roller mill. The resulting solution was a viscous, but more flowable liquid polymer which was at that point a drug-free polymer/solvent composition. The active pharmaceutical ingredient (drug) (e.g., testosterone, testosterone cypionate, testosterone undecanoate, referring to this Example 3 and also Examples 5, 7 and 13 below) was added to the polymer solution and mixed until homogenously dispersed.

Three different test compositions of the invention were made using this new liquid polymer as described above and using testosterone as the test drug. Test Composition A contained a liquid polymer having a molecular weight of 8 kDa and had a composition of 30% liquid polymer, 30% NMP solvent, and 40% Testosterone. Test Composition B contained a liquid polymer having a molecular weight of 22 kDa and had a composition of 30% liquid polymer, 30% NMP solvent, and 40% Testosterone. Test Composition C contained a liquid polymer having a molecular weight of 15 kDa and had a composition of 30% liquid polymer, 40% testosterone, and 30% solvent that was a 30/70 mixture of NMP and benzyl benzoate.

Example 4: Release Profiles from Compositions of the Invention Containing Testosterone Castrated male rats were divided into 3 groups, which were tested with Test Compositions A to C described in Example 3. Each rat received a subcutaneous injection of 100 mg/kg testosterone equivalent of the appropriate composition. Serum levels of testosterone were measured at intervals of approximately 7 days over a period of at least 80 days. Briefly, blood samples were collected and processed for measurement of serum testosterone concentrations by liquid chromatography/mass spectroscopy (LC/MS) at pre-dose, 30 minutes, 1, 3 and 10 hours and days 1, 3, 7, 10, 14, 17, 21, 24, 28, 31, 35, 42, 49, 56, 63, 70, 77, 84, 92, 108, and 120 post-dose, or at days otherwise indicated in subsequent Examples. Results of this experiment are shown in FIG. 2.

As shown in FIG. 2, each of the 3 test groups showed an initial burst release spike in testosterone level shortly after injection, followed by levels of testosterone between approximately 5 ng and approximately 20 ng until at least day 60 (Test Composition A (■), Test Composition B (♦), Test Composition C (▲)).

Therapeutic levels of testosterone of at least 3 ng/ml were maintained 60 days in all test compositions of the present invention, in contrast to the 21 days obtained with similar compositions of the prior art. This result was surprising because the test formulations of the invention utilized a carboxylic acid (i.e., glycolic acid) as a polymer initiator, which initiator is significantly more hydrophilic than the dodecanol initiator disclosed in the '640 patent. Because it would be expected that a faster release rate would be obtained with a more hydrophilic polymer, as disclosed in '640, one skilled in the art would not expect that use of the carboxylic acid initiated polymer system of the present application would provide for a greatly extended duration of release.

However, the tests shown in Examples 1 to 4 establish that a liquid polymer delivery system containing a carboxylic acid initiated polymer surprisingly provides an unexpectedly long duration of release of a drug, such as a hydrophobic drug like a steroid drug such as testosterone. Additional tests in which a hydrophobic drug such as testosterone is replaced by its more hydrophobic ester were conducted in order to attempt to minimize or eliminate the initial burst release seen in the above examples.

Example 5: Compositions of the Invention Containing a Testosterone Ester

75/25 DL-Lactide/Caprolactone liquid polymers (75% DL-lactide and 25% ε-caprolactone) were made using the methods as described in Example 3 above utilizing glycolic acid as a polymer initiator. This polymer was combined, as described in Example 3, with a solvent to provide a drug-free polymer/solvent delivery system.

Three different test compositions of the invention were made substantially as described above and using testosterone cypionate as the test drug. Test Composition D contained a liquid polymer having a molecular weight of 22 kDa and had a composition of 30% liquid polymer, 50% NMP solvent, and 20% testosterone cypionate. Test Composition E contained a liquid polymer having a molecular weight of 25 kDa and had a composition of 30% liquid polymer, 45% NMP solvent, and 25% testosterone cypionate. Test Composition F contained a liquid polymer having a molecular weight of 25 kDa and had a composition of 30% liquid polymer, 50% NMP solvent, and 20% testosterone cypionate.

Example 6: Release Profiles from Testosterone Cypionate Compositions of the Invention Castrated male rats were divided into 3 groups, which were tested with Test Compositions D (FIG. 3, (■)), E (FIG. 3, (♦)) or F (FIG. 3, (▲)) as described in Example 5. Each rat received a subcutaneous injection of 70 mg/kg testosterone equivalent of the appropriate composition. Serum levels of testosterone were measured as described in Example 4 at intervals of approximately 7 days over a period of at least 80 days. Results are shown in FIG. 3.

As shown in FIG. 3, none of the 3 groups injected with the liquid polymer/solvent/testosterone ester composition showed an initial burst release spike in testosterone level after injection. Rather, in all three cases, testosterone levels rose quickly for the first several days following injection, reaching a peak at approximately day 18, and then decreasing until approximately day 60.

Example 7: Compositions of the Invention Containing a Testosterone Ester

75/25 DL-Lactide/Caprolactone liquid polymers (75% DL-lactide and 25% ε-caprolactone) were made as described in Example 3 above utilizing glycolic acid as a polymer initiator. This polymer was combined, as described in Example 3, with a solvent to provide a drug-free polymer/solvent.

Four different test compositions of the invention were made substantially as described above and using testosterone undecanoate as the test drug. Test Composition G contained a liquid polymer having a molecular weight of 8 kDa and had a composition of 20% liquid polymer, 60% NMP solvent, and 20% testosterone undecanoate. Test Composition H contained a liquid polymer having a molecular weight of 8 kDa and had a composition of 30% liquid polymer, 50% NMP solvent, and 20% testosterone undecanoate. Test Composition I contained a liquid polymer having a molecular weight of 22 kDa and had a composition of 20% liquid polymer, 60% NMP solvent, and 20% testosterone undecanoate. Test Composition J contained a liquid polymer having a molecular weight of 22 kDa and had a composition of 30% liquid polymer, 50% NMP solvent, and 20% testosterone undecanoate.

Example 8: Release Profiles from Testosterone Undecanoate Compositions of the Invention Castrated male rats were divided into 4 groups, which were tested with one of Test Compositions G, H, I or J described in Example 7. Each rat received a subcutaneous injection of 70 mg testosterone equivalent of the appropriate composition. Serum levels of testosterone were measured as described in Example 4 at intervals of approximately 7 days over a period of at least 80 days. Results are shown in FIG. 4.

As shown in FIG. 4, none of the 4 groups injected with the liquid polymer/solvent/testosterone ester composition showed an initial burst release spike in testosterone level after injection (Test Composition G (■), Test Composition H (♦), Test Composition I (▲), and Test Composition J (●)). Rather, in all cases, testosterone levels rose quickly for the first several days following injection, reaching a peak at approximately day 18, and then decreasing until approximately day 80.

The tests shown in Examples 5 to 8 establish that a liquid polymer delivery system containing a carboxylic acid initiated polymer surprisingly provides an unexpectedly long duration of release of an ester of a hydrophobic drug, such as a steroid drug like testosterone. The combination of the liquid polymer delivery system with the polymer having carboxylic acid end groups and the ester form of a hydrophobic drug provided a similar long duration of release of drug, but without a burst release of drug from the delivery system.

Example 9: Comparison of Invention to Prior Art Utilizing a Peptide Drug

A test was performed to compare release of peptide drug from the prior art liquid polymer composition of Example 1 and the liquid polymer composition of the invention of Example 3. Specifically, a leuprolide acetate solution and a liquid polymer solution containing 75% DL-lactide and 25% ε-caprolactone produced using the methods described in Example 1 (liquid polymer containing 75% DL-lactide and 25% ε-caprolactone initiated with dodecanol, e.g., as in Test Composition 5 of Example 1, except that the drug is a peptide, leuprolide acetate, in this Example 9) or Example 3 (liquid polymer containing 75% DL-lactide and 25% ε-caprolactone initiated with glycolic acid, e.g., as in Test Composition A of Example 3, except that the drug is the peptide, leuprolide acetate, in this Example 9) were mixed and weighed into a vial to form compositions containing 30% liquid polymer, 58% w/w NMP and 12% w/w leuprolide acetate.

Room temperature phosphate buffered saline (PBS) was added to the vials. The vials were placed in an orbital incubator shaker at 37° C. and 125 rpm. 1 mL of PBS was removed for analysis at selected time points and replaced with fresh buffer. An in vitro release study was performed in PBS pH 7.4 and the percentage of leuprolide acetate released from the liquid polymer compositions was measured by high performance liquid chromatography (HPLC). Results are shown in FIG. 5, where the drug release over time from the prior art liquid polymer initiated with dodecanol (♦) is compared to the drug release over time from the liquid polymer of the invention initiated with glycolic acid (■).

As shown in FIG. 5, release of peptide drug occurred from the prior art composition in an immediate spike during the first day following administration, and essentially no more drug was released following this initial spike.

In contrast, no spike release occurred from the composition of the present invention. Rather, a steady release of peptide drug was obtained over a period of 63 days (1512 hours), following which drug release slowed.

Example 10: Preparation of 14 kDa Liquid Polymer Solutions in NMP Containing Leuprolide Acetate 75/25 DL-lactide/caprolactone liquid polymers (75% DL-lactide and 25% ε-caprolactone) were made as described in Example 3 above utilizing glycolic acid as a polymer initiator. This polymer was combined, as described in Example 3, with a solvent to provide a drug-free polymer/solvent composition. The polymer/solvent compositions were then combined with a peptide drug, leuprolide acetate (LA) solution to form the compositions used in this example.

More specifically, using the methods as generally described in Example 3, 75% DL-lactide and 25% ε-caprolactone liquid polymer compositions were prepared and combined with NMP solvent. Also as described in Example 3, weight average molecular weight of the polymers was determined with by gas permeation chromatography (GPC) with a refractive index detector (e.g., Agilent 1260 Infinity Quaternary LC with Agilent G1362A Refractive Index Detector). In this example, liquid polymers having a weight average molecular weight of 14 kDa were produced.

Leuprolide acetate (LA) (4.5 grams) was dissolved in 5.5 grams of NMP (45/55 w/w leuprolide acetate solution in NMP). Complete dissolution required mixing with speed mixer or roller mill at room temperature. The two compositions (polymer/solvent and drug/solvent) are then mixed just prior to use (e.g., injection or in vitro release assay), for example, by using a dual chambered single syringe or two different syringes, and then weighed into a vial. For in vitro release studies, as described in Example 9 and in Example 11 below, room temperature PBS was added to the vial. The vial was placed in an orbital incubator shaker at 37° C. and 125 rpm. 1 mL of PBS was removed for analysis at selected time points and replaced with fresh buffer.

Three compositions containing: leuprolide acetate, a liquid polymer having a molecular weight of 14 kDa and a solvent (NMP) were made. Each composition contained leuprolide acetate at a concentration of 12% w/w. Composition K contained polymer at a concentration of 30% and NMP at a concentration of 58%. Composition L contained polymer at a concentration of 35% and NMP at a concentration of 53%. Composition M contained polymer at a concentration of 40% and NMP at a concentration of 48%. The compositions were made by combining an amount of the liquid polymer obtained in Example 3 (liquid polymer containing 75% DL-lactide and 25% ε-caprolactone initiated with glycolic acid) with the appropriate amount of solvent as indicated above, and then combining with leuprolide acetate.

Example 11: Release Profiles from 14 kDa Liquid Polymer Compositions with Leuprolide An in vitro release study as described in Example 9 (i.e., determined by HPLC in phosphate buffered saline (PBS) pH 7.4) was performed. In this study, the compositions K, L and M of Example 10 were tested for in vitro release of leuprolide acetate. Results are shown in FIG. 6. As shown in FIG. 6, release of peptide drug was similar from all tested compositions. Release was observed to be faster from compositions that contained a lower concentration of liquid polymer and higher concentration of solvent. Release was fastest from Composition K (♦) (polymer at a concentration of 30% and NMP at a concentration of 58%) and slowest from Composition M (▲) (polymer at a concentration of 40% and NMP at a concentration of 48%), and continued steadily during the 1600 hours (66 days) of the study. The pattern of release from each of Compositions K (♦), L (■), and M (▲) was similar.

Example 12: 8 kDa Liquid Polymer Solutions in NMP Containing Leuprolide Acetate

75/25 DL-lactide/caprolactone liquid polymers (75% DL-lactide and 25% ε-caprolactone) were made as described in Example 3 above utilizing glycolic acid as a polymer initiator. This polymer was combined, as described in Example 3, with a solvent to provide a drug-free polymer/solvent composition. The polymer/solvent compositions were then combined with a peptide drug, leuprolide acetate (LA) solution, as described in Example 10 to form the compositions used in this example. In this example, the liquid polymers had a weight average molecular weight of 8 kDa.

Three compositions containing leuprolide acetate, a liquid polymer having a molecular weight of 8 kDa, and a solvent (NMP) were made. Each composition contained leuprolide acetate at a concentration of 12% w/w. Composition N contained polymer at a concentration of 30% and NMP at a concentration of 58%. Composition O contained polymer at a concentration of 35% and NMP at a concentration of 53%. Composition P contained polymer at a concentration of 40% and NMP at a concentration of 48%. The compositions were made by combining an amount of the liquid polymer obtained in Example 3 (liquid polymer containing 75% DL-lactide and 25% ε-caprolactone initiated with glycolic acid) with the appropriate amount of solvent as indicated above, and then combining with leuprolide acetate as generally described in Example 10.

Example 13: Release Profiles from 8 kDa Liquid Polymer Compositions with Leuprolide An in vitro release study as described in Example 9 was performed. In this study, the compositions of N, O and P from Example 12 were tested for in vitro release of leuprolide acetate. Results are shown in FIG. 7.

As shown in FIG. 7, release of peptide drug was similar from all tested compositions. Release was observed to be slightly faster from compositions that contained a lower concentration of liquid polymer and higher concentration of solvent. Release from all compositions was steady during the 1600 hours (66 days) of the study. The pattern of release from each of Compositions N (■), O (▲), and P (●) was similar. Additionally, release from the compositions of Example 12 was somewhat more rapid than from the compositions of Example 10 (see FIG. 6). However, this difference does not appear to be significant.

Example 14: 22 kDa Liquid Polymer Solutions in NMP Containing Testosterone

This example evaluated the use of alternative liquid polymer compositions and alternative carboxylic acid initiators as a further demonstration of the formulations and methods of the present invention. Specifically, a 75/25 DL-lactide/caprolactone liquid polymer (75% DL-lactide and 25% ε-caprolactone) was made as described in Example 3 above, except that lactic acid was used as the polymer initiator. In addition, a 75/25 DL-lactide/trimethylene carbonate (TMC) liquid polymer (75% DL-lactide/25% trimethylene carbonate (TMC) polymer) was also produced using the methods as generally described in Example 3, using glycolic acid as the polymer initiator. Each of these polymers was combined, as described in Example 3, with a solvent (NMP) to provide a drug-free polymer/solvent composition, and then each of these polymer/solvent compositions was further combined with testosterone undecanoate using the methods generally described in Example 3.

Two test compositions containing testosterone undecanoate, a liquid polymer having a molecular weight of 22 kDa, and a solvent (NMP) were made. Each composition contained testosterone undecanoate at a concentration of 20 wt %. Composition Q contained a 75% DL-lactide/25% ε-caprolactone polymer initiated with lactic acid at a concentration of 30 wt % and NMP at a concentration of 50 wt %. Composition R contained a 75% DL-lactide/25% trimethylene carbonate (TMC) polymer initiated with glycolic acid at a concentration of 30 wt % and NMP at a concentration of 50 wt %. A control formulation contained a 75% DL-lactide/25% ε-caprolactone polymer initiated with glycolic acid at a concentration of 30 wt % and NMP at a concentration of 50 wt % (corresponding to Composition J from Example 7).

Example 15: Release Profiles from 22 kDa Liquid Polymer Compositions with Testosterone Castrated male Sprague Dawley rats were divided into 2 groups, which were tested, respectively, with Test Compositions Q and R described in Example 14. Each rat received a subcutaneous injection of the appropriate composition to deliver a target dose of 34 mg of testosterone undecanoate. Serum levels of testosterone were measured at intervals of approximately 7 days over greater than 120 days. Briefly, blood samples were collected and processed for measurement of serum testosterone concentrations by liquid chromatography/mass spectroscopy (LC/MS/MS) at pre-dose, and at intervals beyond 120 days post-dose. Results are shown in FIGS. 8A and 8B (Control Composition (equivalent to Composition J from Example 7) (▲); Test Composition Q (■); Test Composition R (♦)). FIG. 8A shows testosterone release (ng/mL) as non-normalized data from this experiment, and FIG. 8B shows testosterone release (ng/mL per mg/kg) as data normalized for both the amount of formulation received by individual animals and for individual animal body weight.

As shown in FIGS. 8A and 8B, the release of testosterone from the Test Compositions Q and R was similar in magnitude and pattern to the Control Composition. In all cases, testosterone levels rose quickly for the first several days following injection, reaching a peak at approximately day 18, and then decreasing gradually over an extended time. Test Compositions Q and R were continuing to release testosterone past the 126-day time point. This example again demonstrates that a liquid polymer delivery system containing a liquid polymer with carboxylic acid end groups of the invention surprisingly provides an unexpectedly long duration of release of a drug in vivo, such as testosterone undecanoate. In addition, this example shows that the liquid polymer composition of the invention is not limited to polymers formed from DL-lactide and ε-caprolactone, and that the carboxylic acid end group is not limited to end groups formed by a glycolic acid initiator (i.e., that a variety of liquid polymers and a variety of initiators that add carboxylic acid end groups are useful according to the invention).

Various modifications of the above described invention will be evident to those skilled in the art. It is intended that such modifications are included within the scope of the following claims.

The invention claimed is:
1. A liquid polymer composition for administration into the body of an animal, comprising:
 a. a biodegradable liquid polyester comprising at least one carboxylic acid end group;
 b. a biocompatible organic solvent; and
 c. an active pharmaceutical agent;
 wherein:
 the biodegradable liquid polyester comprises at least about 50% lactide monomer residues, and an amount greater than about 5% of residues of comonomers selected from caprolactone, trimethylene carbonate and combinations thereof;

the biodegradable liquid polyester has a weight-average molecular weight between about 5 kDa and about 40 kDa; and the duration of release of the active pharmaceutical agent from the composition is longer than the duration of release obtained from a biodegradable liquid polyester without at least one carboxylic acid end group.

2. The liquid polymer composition of claim 1, wherein the carboxylic acid is selected from the group consisting of GABA (gamma-amino butyric acid), GHB (gamma-hydroxybutyric acid), lactic acid, glycolic acid, citric acid, and undecylenic acid.

3. The liquid polymer composition of claim 1, wherein the biodegradable liquid polyester comprises about 75% lactide monomer residues.

4. The liquid polymer composition of claim 1, wherein the biodegradable liquid polyester comprises an amount greater than about 5% and less than about 50% of residues of comonomers selected from caprolactone, trimethylene carbonate and combinations thereof.

5. The liquid polymer composition of claim 1, wherein the biodegradable liquid polyester comprises about 25% of residues of comonomers selected from caprolactone, trimethylene carbonate and combinations thereof.

6. The liquid polymer composition of claim 1, wherein the biodegradable liquid polyester is selected from the group consisting of 75:25 lactide:caprolactone and 75:25 lactide:trimethylene carbonate.

7. The liquid polymer composition of claim 1, wherein the biocompatible organic solvent comprises one or more organic solvents selected from the group consisting of amides, acids, alcohols, esters of monobasic acids, ether alcohols, sulfoxides, lactones, polyhydroxy alcohols, esters of polyhydroxy alcohols, ketones, and ethers.

8. The liquid polymer composition of claim 1, wherein the biocompatible organic solvent comprises one or more organic solvents selected from the group consisting of N-methyl-2-pyrrolidone (NMP), 2-pyrrolidone, N-ethyl-2-pyrrolidone, N-cyclohexyl-2-pyrrolidone, N-hydroxyethyl-2-pyrrolidone, dimethyl acetamide, dimethyl formamide, acetic acid, lactic acid, ethanol, propanol, methyl lactate, ethyl lactate, methyl acetate, diethylene glycol monomethyl ether, glycofurol, glycerol formal, isopropylidene glycerol, dimethyl sulfoxide, ε-caprolactone, butyrolactone, propylene glycol, polyethylene glycol, glycerol, 1,3-butyleneglycol, methoxypolyethylene glycol, methoxypropylene glycol, acetone, methyl ethyl ketone, and tetrahydrofuran.

9. The liquid polymer composition of claim 1, wherein the composition comprises between about 20 wt % and about 40 wt % biodegradable liquid polyester and between about 40 wt % and about 60 wt % biocompatible organic solvent.

10. The liquid polymer composition of claim 1, wherein the active pharmaceutical agent is present in a dosage effective for one week or greater.

11. The liquid polymer composition of claim 1, wherein the active pharmaceutical agent is present in a dosage effective for one month or greater.

12. The liquid polymer composition of claim 1, wherein the active pharmaceutical agent is present in an amount between 1% and 50% by weight of the composition.

13. The liquid polymer composition of claim 12, wherein the active pharmaceutical agent is present in an amount between about 1 wt % and about 25 wt %.

14. The liquid polymer composition of claim 12, wherein the active pharmaceutical agent is present in an amount between about 25 wt % and about 50 wt %.

15. The liquid polymer composition of claim 1, wherein the active pharmaceutical agent is a hydrophobic small molecule drug.

16. The liquid polymer composition of claim 15, wherein the hydrophobic small molecule drug is selected from the group consisting of corticosteroids, azole medications, sex steroids, statin drugs, and antiandrogen drugs.

17. The liquid polymer pharmaceutical composition of claim 1, wherein the active pharmaceutical agent is leuprolide (leuprorelin) or a pharmaceutically acceptable salt or ester thereof.

18. The liquid polymer composition of claim 1, wherein the biocompatible organic solvent comprises one or more biocompatible organic solvents that have a water solubility of 10% or higher by weight of the solvent in water.

19. A method of delivering an active pharmaceutical agent to a body, comprising injecting the liquid polymer pharmaceutical composition of claim 1 into the body.

20. The method of claim 19, wherein a biodegradable, non-solid implant is formed in situ in the body.

21. The liquid polymer composition of claim 1, wherein the biocompatible organic solvent comprises N-methyl-2-pyrrolidone.

22. The liquid polymer composition of claim 1, wherein the active pharmaceutical agent is testosterone or a pharmaceutically acceptable salt or ester thereof.

23. The liquid polymer composition of claim 22, wherein the active pharmaceutical agent is testosterone undecanoate.

24. The liquid polymer composition of claim 1, wherein the composition comprises between about 20 wt % and about 40 wt % biodegradable liquid polyester, between about 40 wt % and about 60 wt % biocompatible organic solvent, and between about 10 wt % and about 30 wt % active pharmaceutical agent.

25. The liquid polymer composition of claim 1, wherein, after administration, the biocompatible organic solvent dissipates in the body of the animal and the biodegradable liquid polyester forms a biodegradable, non-solid implant in situ in the body of the animal.

26. The liquid polymer composition of claim 1, wherein the biodegradable liquid polyester has a weight-average molecular weight between about 8 kDa and about 25 kDa.

27. The liquid polymer composition of claim 1, wherein the biodegradable liquid polyester is a copolymer of two monomers having a molar ratio of lactide to caprolactone or trimethylene carbonate between about 25:75 and about 75:25.

28. A delivery system for administration of a liquid polymer pharmaceutical composition, comprising:
  a. a syringe component;
  b. a formulation component comprising a biodegradable liquid polyester comprising at least one carboxylic acid end group and a biocompatible organic solvent; and
  c. an active pharmaceutical agent;
  wherein:
  the formulation component and the active pharmaceutical agent are contained within the syringe component,
  the biodegradable liquid polyester comprises at least about 50% lactide monomer residues, and an amount greater than about 5% of residues of comonomers selected from caprolactone, trimethylene carbonate and combinations thereof;
  the biodegradable liquid polyester has a weight-average molecular weight between about 5 kDa and about 40 kDa; and
  the duration of release of the active pharmaceutical agent from the composition is longer than the duration of release obtained from a biodegradable liquid polyester without at least one carboxylic acid end group.

29. The delivery system of claim 28, wherein the syringe component is a single syringe containing the formulation component and active pharmaceutical agent.

30. The delivery system of claim 28, wherein the syringe component is a two syringe system wherein a first syringe of the two syringe system contains the formulation component and a second syringe of the two syringe system contains the active pharmaceutical agent.

31. A liquid polymer composition for administration into the body of an animal or human comprising:
  a. a biodegradable liquid polymer having a carboxylic acid end group,
  b. a biocompatible organic solvent, and
  c. a therapeutically effective amount of a drug,
  wherein:
  the biodegradable liquid polyester comprises at least about 50% lactide monomer residues, and an amount greater than about 5% of residues of comonomers selected from the group consisting of caprolactone, trimethylene carbonate and combinations thereof;
  the biodegradable liquid polyester has a weight-average molecular weight between about 5 kDa and about 40 kDa; and
  the duration of release of the drug from the composition is longer than the duration of release obtained from a biodegradable liquid polyester without at least one carboxylic acid end group.

* * * * *

UNITED STATES PATENT AND TRADEMARK OFFICE
CERTIFICATE OF CORRECTION

PATENT NO. : 10,786,515 B2
APPLICATION NO. : 15/749030
DATED : September 29, 2020
INVENTOR(S) : John Milton Downing, Vipin Saxena and John Middleton It is certified that error appears in the above-identified patent and that said Letters Patent is hereby corrected as shown below:

In the Claims

Claim 17, Column 28, Line 8, delete "The liquid polymer pharmaceutical composition of..." and insert -- The liquid polymer composition of... --

Signed and Sealed this
Twenty-second Day of December, 2020

Andrei Iancu
*Director of the United States Patent and Trademark Office*